(12) United States Patent
Flynn et al.

(10) Patent No.: US 6,673,788 B2
(45) Date of Patent: Jan. 6, 2004

(54) ELECTROPHILIC KETONES FOR THE TREATMENT OF HERPESVIRUS INFECTIONS

(75) Inventors: Daniel L. Flynn, Clarkson Valley, MO (US); Jeffery Zablocki, Lafayette, CO (US); Kenneth Williams, Evanston, IL (US); Susan L. Hockerman, Chicago, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 10/303,596

(22) Filed: Nov. 25, 2002

(65) Prior Publication Data

US 2003/0119721 A1 Jun. 26, 2003

Related U.S. Application Data

(62) Division of application No. 09/712,002, filed on Nov. 14, 2000, which is a continuation of application No. 09/221,016, filed on Dec. 23, 1998, now abandoned, which is a continuation of application No. 08/620,681, filed on Mar. 19, 1996, now abandoned.

(51) Int. Cl.[7] .................. A61K 31/33; A61K 31/27; A61K 31/245; A61K 31/13
(52) U.S. Cl. .................. 514/183; 514/476; 514/535; 514/538; 514/646; 514/678; 514/688
(58) Field of Search .................. 514/183, 476, 514/535, 538, 646, 678, 688

(56) References Cited

FOREIGN PATENT DOCUMENTS

| EP | 298020 | * | 1/1989 |
| EP | 337701 | * | 10/1989 |

* cited by examiner

Primary Examiner—Mukund J. Shah
Assistant Examiner—Sudhaker B. Patel
(74) Attorney, Agent, or Firm—Joseph W. Bulock; Rachel A. Polster

(57) ABSTRACT

A class of compounds is described which can be used for the treatment of viral infections. Compounds of particular interest are defined by Formula II:

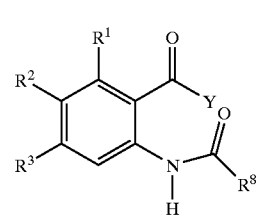

wherein each of $R^1$, $R^2$, and $R^3$ is independently selected from hydrido, halo, and nitro; wherein $R^8$ is selected from haloalkyl, optionally substituted aryl, optionally substituted aralkyl, optionally substituted heteroaryl, optionally substituted arylalkoxy and optionally substituted aryloxyalkyl; wherein Y is selected from fluoroalkyl, and

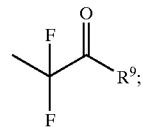

and wherein $R^9$ is alkylamino; or a pharmaceutically-acceptable salt or tautomer thereof.

26 Claims, No Drawings

ELECTROPHILIC KETONES FOR THE TREATMENT OF HERPESVIRUS INFECTIONS

This Application is a divisional of U.S. Ser. No. 09/712,002, filed Nov. 14, 2000, which is a continuation of application Ser. No. 09/221,016 filed on Dec. 23, 1998 now abandoned, which is a continuation of application Ser. No. 08/620,681, filed Mar. 19, 1996, now abandoned.

FIELD OF THE INVENTION

This invention is in the field of antiviral agents and specifically relates to compounds, compositions and methods for treating herpesvirus infections.

BACKGROUND OF THE INVENTION

There is a great need for new therapies active in the treatment of viral diseases. Whereas there has been great progress in developing a variety of therapies for the treatment of bacterial infections, there are few viable therapies for the treatment of herpesvirus. ganciclovir, aciclovir and foscarnet are currently utilized for the treatment of herpesvirus infections, however, these therapies can have substantial side effects based on their deleterious effects on host cell DNA replication. They also affect a limited number of viral infections. In addition, viruses are known to develop resistance to therapies, and such resistance causes a progressive decline in efficacy.

Viruses are classified into broad categories based on whether they incorporate RNA or DNA. Important virus families classified of RNA type include orthomyxoviridae, paramyxoviridae, picornaviridae, rhabdoviridae, coronaviridae, togaviridae, bunyaviridae, arenaviridae and retroviridae. Important virus families classified of DNA type include adenoviridae, poxviridae, papovaviridae and herpesviridae.

Herpesviridae is a family of DNA viruses which include herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

It is known that herpesvirus replicate by directing the synthesis of a number of proteins encoded by the herpesvirus DNA in the host cell. One of the important virus-encoded proteins is made as a fusion protein precursor consisting of an amino terminal-located protease and carboxyl terminal-located capsid assembly protein. This precursor is proteolytically processed in an autocatalytic manner at a specific amino acid sequence known as the "release" site, yielding separate protease and capsid assembly protein. The capsid assembly protein is cleaved further by the protease at another specific amino acid sequence known as the "maturation" cleavage site. U.S. Pat. No. 5,478,727, to Roizman and Liu, describes a virus-specific serine protease which has a role in HSV replication. Liu and Roizman [*J. Virol,* 65, 5149 (1991)] describe the sequence and activity of a protease and the associated assembly protein encoded by $U_L26$ of HSV-1. Recently, U.S. Pat. No. 5,434,074, to W. Gibson and A. Welch, describes a simian CMV protease. A. Welch et al. [*Proc. Natl. Acad. Sci. USA,* 88, 10792 (1991)] describe the related protease (also known as assemblin) and assembly protein encoded by $U_L80$ of a human CMV. An approach currently being investigated for potential use in the treatment of herpesvirus infections is the development of inhibitors of herpesvirus proteases.

Arylketones containing a tetrazolylcarbonylamino substituent have been described. European publication EP 337,701, published Apr. 11, 1988, describes the use of 3-acetyl-5-fluoro-2-hydroxytetrazole-5-carboxanilide for treating autoimmune disorders or arthritis.

Substituted arylureas have been described in European publication EP 355,819, published Feb. 28, 1990, as high intensity sweeteners.

Aryltrihalomethylketones combined with hydrogen peroxide have been described in European patent publication EP 298,020, published Jan. 4, 1989, as reagents for epoxidation of steroids. German patent document DE 4,201,435, describes a method of preparing trifluoromethylketones from the alcohols.

U.S. Pat. No. 4,855,460, to M. Tordeux et al., describes the formation of simple pseudoacids via perfluoroalkylation of acid anhydrides. Specifically, trifluoroacetophenone is described.

WO 92/18475, published Oct. 29, 1992, describes phenylsubstituted pyrrolidines as dopamine receptor agonist/antagonists. Aryltrifluoromethylcarbinols have been described in U.S. Pat. No. 4,285,943, issued to M. Vincent et al., as analgesic, antipyretic, and anti-inflammatory agents.

Inhibition of serine proteases by electrophilic carbonyl derivatives, in particular peptidyl derivatives possessing an electrophilic carbonyl or boron group, is a well documented process. Early work describes where the $P_1$ cleavage site is mimicked by an electrophilic aldehyde, alpha-ketoester, trifluoromethylketone, alphaketoamide, or boronic ester. [See J. Powers and J. Wade Harper, "*Inhibitors of Serine Proteases*", in Proteinase Inhibitors, 55–152 (1986); R. Wiley and D. Rich, *Medicinal Research Reviews,* 13, 327–384 (1993).]

For example, the compounds in European patent publication EP 276,101, published Jul. 27, 1988, are described as inhibiting human leukocyte elastase (HLE). Generally, the inhibitors consist of a proline-based peptidyl sequence which is terminated by a trifluoromethylketone. European publication EP 249,349, published Dec. 16, 1987, describes a proline-derived peptide sequence terminated by a 2,2-difluoro-3-phenyl-1,3-dicarbonyl group. European publication EP 204,571, published Dec. 12, 1986, describes a proline-derived peptide sequence consisting of one-three amino acids and terminated by a 2,2-difluoro-3-phenyl-1,3-dicarbonyl group.

Several references have described aryltrifluoromethylketones as inhibitors of acetylcholinesterase, a serine esterase. European publication EP 403,713, published Dec. 27, 1990, describes m-(silyl)phenylfluoroketones in treatment of Alzheimers disease and senile dementia. U.S. Pat. No. 5,166,181 describes [m-(alkylaminoalkyl)aryl]-haloketone compounds as acetylcholinesterase inhibitors. Specifically, 1-[3-[1-(N,N-dimethylamino)ethyl]phenyl]-2,2,2-trifluoroethanone is described.

Halosubstituted acetophenones have not previously been described as selective herpesvirus protease inhibitors or for the treatment and/or prophylaxis of herpesvirus infection.

DESCRIPTION OF THE INVENTION

The present invention relates to a class of halo-substituted acetophenones, useful in the therapeutic and prophylactic treatment of viral infections, as defined by Formula I:

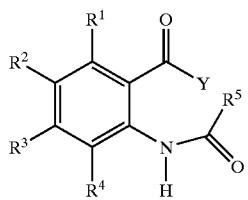

wherein each of $R^1$, $R^2$, $R^3$, and $R^4$ is independently selected from hydrido, alkyl, aralkyl, halo, alkoxy, cyano, nitro, amino, alkylamino, N-acylamino, alkylsulfonyloxy, aminosulfonyl, N-(haloalkylcarbonyl)amino, peptidyl, amino acid residue,

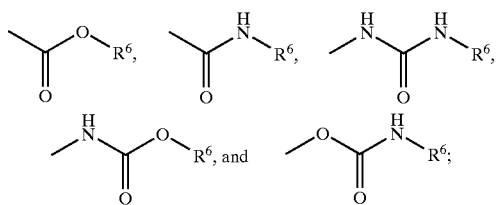

wherein $R^5$ is selected from alkoxy, aryloxy, aralkyloxy, alkylthio, arylthio, aralkylthio, alkylamino, arylamino, aralkylamino, alkyl, aryl, aralkyl, heterocyclyl, and heterocyclylalkyl, wherein $R^5$ is optionally substituted at a substitutable position with one or more substituents selected from alkyl, alkoxy, aryloxy, alkylthio, arylthio, halo, nitro, N-acylamino, amino, alkylamino, alkoxycarbonyl, amino acid residue and peptidyl;

wherein $R^6$ is selected from alkyl, aryl, aralkyl, heterocyclyl and heterocyclylalkyl, wherein $R^6$ is optionally substituted at a substitutable position with a radical selected from alkoxy, aryloxy, alkylthio, arylthio, halo, nitro, N-acylamino, amino, alkylamino and alkoxycarbonyl;

wherein Y is selected from fluoroalkyl and

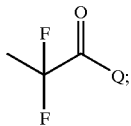

wherein Q is selected from alkoxy, aryloxy, aralkyloxy, amino acid residue, peptidyl, and —$NHR^7$; and wherein $R^7$ is a radical selected from alkyl, aralkyl, and heterocyclylalkyl, wherein $R^7$ is optionally substituted at a substitutable position with a radical selected from amino, nitrogen-containing heterocyclyl and alkylamino;

or a pharmaceutically-acceptable salt or tautomer thereof.

The compounds of this invention have been shown to be particularly effective against herpetoviridae. Thus they are particularly useful for the treatment of herpes simplex viruses (HSV-1, HSV-2), cytomegalovirus (CMV), varicella-zoster virus (VZV), Epstein-Barr (EBV), human herpesvirus-6 (HHV-6), human herpesvirus-7 (HHV-7), human herpesvirus-8 (HHV-8), pseudorabies and rhinotracheitis, among others.

The invention further involves a method of treating a subject having a viral infection with an effective amount of a compound of Formula I. Preferably, the subject is treated with a herpesvirus protease inhibitor. More preferred is a method wherein the viral protease inhibitor is a CMV protease inhibitor, EBV protease, VZV protease or an HSV protease inhibitor. Even more preferred is a method wherein the subject is treated with an inhibitor of CMV protease, encoded by $U_L80$, HSV-1 protease or HSV-2 protease encoded by $U_L26$, such as the halosubstituted acetophenone compounds of the present invention.

Besides being useful for human treatment, these compounds are also useful for veterinary treatment of animals, including companion animals and farm animals, such as, but not limited to, horses, dogs, cats, cows, fish, sheep and pigs.

The present compounds may also be used in co-therapies, partially or completely, in place of other conventional antiviral compounds, such as together with antivirals including but not limited to ganciclovir, docosanol, trifluridine, foscarnet, ribavirin, epervudine, interferon, thymostimulin, Ciba-Geigy CGP-16056, sprofen, Efalith, ibuprofen piconol, ufenamate, thymopentin, aciclovir, valaciclovir, edoxudine, famciclovir, idoxuridine, vidarabine, Epavir, zinc acetate, tromantadine, riodoxol, sorivudine, Yakult Honsha LC-9018, cidofovir, bromovinyldeoxyuridine, Lidakol, Stega Pharmaceutical cytokine-releasing agent, CSL ISCOM, penciclovir, Viraplex, Pharmacia & Upjohn THF, Boehringer Ingelheim BIRR-4, NIH peptide T, Virend, zinc glycerolate, and lobucavir.

A preferred class of compounds consists of those compounds of Formula I wherein each of $R^1$, $R^2$, $R^3$, and $R^4$ is independently selected from hydrido, lower alkyl, lower aralkyl, halo, lower alkoxy, cyano, nitro, amino, lower alkylamino, N-acylamino, lower alkylsulfonyloxy, aminosulfonyl, lower N-(haloalkylcarbonyl)amino, amino acid residue, peptidyl,

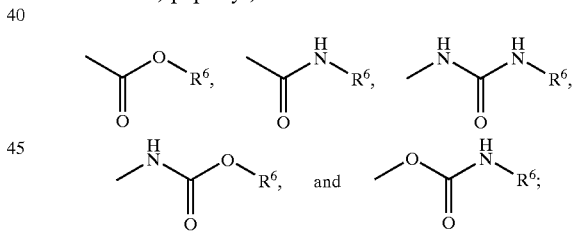

wherein $R^5$ is selected from lower alkoxy, phenyloxy, lower aralkyloxy, lower alkylthio, phenylthio, lower aralkylthio, lower alkylamino, arylamino, lower aralkylamino, lower alkyl, 6–10-membered aryl, lower aralkyl, 5–10-membered heterocyclyl, and lower heterocyclylalkyl, wherein $R^5$ is optionally substituted at a substitutable position with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue and peptidyl; wherein $R^6$ is selected from lower alkyl, 6–10-membered aryl, lower aralkyl, 5–10-membered heterocyclyl and lower heteroaralkyl, wherein $R^6$ is optionally substituted at a substitutable position with a radical selected from lower alkoxy, phenyloxy, lower alkylthio, phenylthio, halo, nitro, N-acylamino, amino, lower alkylamino, and lower alkoxycarbonyl; wherein Y is selected from lower fluoroalkyl and

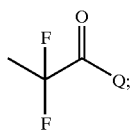

wherein Q is selected from lower alkoxy, phenyloxy, lower aralkyloxy, N-amino acid residue, N-peptidyl, and —NHR$^7$; and wherein R$^7$ is a radical selected from lower alkyl, lower aralkyl, and lower heteroaralkyl, wherein R$^7$ is optionally substituted at a substitutable position with one or more radical selected from amino, 5–6-membered nitrogen-containing heterocyclyl and lower N,N-dialkylamino; or a pharmaceutically-acceptable salt or tautomer thereof.

A more preferred class of compounds consists of those compounds of Formula I wherein Y is lower fluoroalkyl; wherein each of R$^1$, R$^2$, R$^3$, and R$^4$ is independently selected from hydrido, lower alkyl, halo, lower alkoxy, nitro, and amino; and wherein R$^5$ is selected from phenylalkoxy, lower alkyl substituted with halo or phenyloxy, phenyl, lower phenylalkyl, and five–ten membered heteroaryl, wherein R$^5$ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

An even more preferred class of compounds consists of those compounds of Formula I wherein Y is selected from difluoromethyl, trifluoromethyl, pentafluoroethyl, heptafluoropropyl, 1,1-difluoroethyl, and 1,1-difluoropropyl; wherein each of R$^1$, R$^2$, R$^3$, and R$^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; wherein R$^5$ is selected from phenylmethoxy, phenylethoxy, phenylpropoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, phenylethyl, furyl, pyrazinyl, oxazolyl, thiazolyl, thienyl, pyrrolyl, benzothienyl, benzofuranyl, indolyl, and pyridyl, wherein R$^5$ is optionally substituted at a substitutable position of a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, phenyloxy, methylthio, phenylthio, fluoro, chloro, bromo, iodo, nitro, N-formylamino, acetylamino, amino, N,N-dimethylamino and methoxycarbonyl; or a pharmaceutically-acceptable salt or tautomer thereof.

Another more preferred class of compounds consists of those compounds of Formula I wherein Y is

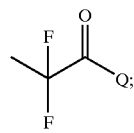

wherein Q is selected from lower alkoxy, phenyloxy, lower aralkyloxy, N-amino acid residue, N-peptidyl, and —NHR$^7$; and wherein R$^7$ is a radical selected from lower alkyl, lower aralkyl, and lower heteroaralkyl, wherein R$^7$ is optionally substituted at a substitutable position with a radical selected from amino, 5–6 membered nitrogen-containing heterocyclyl and lower N,N-dialkylamino; wherein each of R$^1$, R$^2$, R$^3$, and R$^4$ is independently selected from hydrido, lower alkyl, halo, lower alkoxy, nitro, and amino; and wherein R$^5$ is selected from phenylalkoxy, lower alkyl substituted with halo or phenyloxy, phenyl, lower phenylalkyl, and five–ten membered heteroaryl, wherein R$^5$ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

Another even more preferred class of compounds consists of those compounds of Formula I wherein Y is

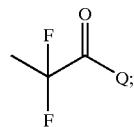

wherein Q is selected from methoxy, ethoxy, propoxy, isopropoxy, butoxy, phenyloxy, benzyloxy, phenylethoxy, and —NHR$^7$; and wherein R$^7$ is a radical selected from methyl, ethyl, n-propyl, isopropyl, n-butyl, isobutyl, sec-butyl, tert-butyl, pentyl, hexyl, benzyl, phenethyl, oxazolylmethyl, oxazolylethyl, imidazolylmethyl, imidazolylethyl, oxazolinylmethyl, oxazolinylethyl, indolylethyl, indolylmethyl, pyridylmethyl, thienylmethyl, and furylethyl, wherein R$^7$ is optionally substituted at a substitutable position with a radical selected from amino, piperidinyl, piperazinyl, pyrrolidinyl, morpholinyl, pyridyl, pyrimidyl and N,N-dimethylamino; wherein each of R$^1$, R$^2$, R$^3$, and R$^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; and wherein R$^5$ is selected from phenylmethoxy, phenylethoxy, phenylpropoxy, fluoromethyl, difluoromethyl, trifluoromethyl, chloromethyl, dichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, phenylethyl, furyl, pyrazinyl, oxazolyl, thiazolyl, thienyl, pyrrolyl, benzothienyl, benzofuranyl, indolyl, and pyridyl, wherein R$^5$ is optionally substituted at a substitutable position on a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, tert-butoxy, phenyloxy, methylthio, phenylthio, fluoro, chloro, bromo, iodo, nitro, N-formylamino, N-acetylamino, amino, N,N-dimethylamino and methoxycarbonyl; or a pharmaceutically-acceptable salt or tautomer thereof.

Another preferred class of compounds consists of those compounds of Formula II wherein

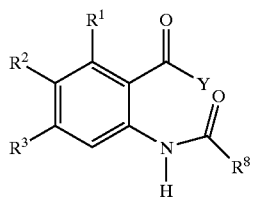

II wherein each of $R^1$, $R^2$, and $R^3$ is independently selected from hydrido, halo, and nitro;
wherein $R^8$ is selected from haloalkyl, optionally substituted aryl, optionally substituted aralkyl, optionally substituted heteroaryl, optionally substituted arylalkoxy and optionally substituted aryloxyalkyl;
wherein Y is selected from fluoroalkyl, and

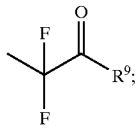

and
wherein $R^9$ is alkylamino;
or a pharmaceutically-acceptable salt or tautomer thereof.

Another preferred class of compounds consists of those compounds of Formula II wherein $R^1$ is selected from hydrido, fluoro, chloro, bromo and iodo; wherein $R^2$ is selected from hydrido, fluoro, chloro, bromo and iodo; wherein $R^3$ is selected from hydrido, fluoro, chloro, bromo, iodo and nitro; wherein $R^8$ is selected from trifluoromethyl, phenyl, phenylmethyl, phenylethyl, furyl, pyridyl, pyrazinyl, thienyl, pyrrolyl, benzothienyl, benzofuranyl, indolyl, phenylmethyloxy, (phenyloxy)propyl and phenyloxymethyl; wherein Y is selected from trifluoromethyl and

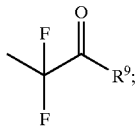

and
wherein $R^9$ is selected from methylamino, ethylamino, propylamino, isopropylamino and N,N-dimethylamino; or a pharmaceutically-acceptable salt or tautomer thereof.

A family of specific compounds of particular interest within Formulas I and II consists of compounds and pharmaceutically-acceptable salts thereof as follows:

α-phenoxy-N-[2-(2,2,2-trifluoro-1-oxoethyl)phenyl]butanamide;

N-[2-(2,2,2-trifluoro-1-oxoethyl)phenyl]furan-2-carboxamide;
N-[5-fluoro-2-(2,2,2-trifluoro-1-oxoethyl)phenyl]benzenepropanamide;
N-[3-chloro-2-(2,2,2-trifluoro-1-oxoethyl)phenyl]benzenepropanamide;
N-[2-(2,2,2-trifluoro-1-oxoethyl)phenyl]benzenepropanamide;
N-[2-(2,2,2-trifluoro-1-oxoethyl)phenyl]pyrazine-2-carboxamide;
phenylmethyl N-[2-(2,2,2-trifluoro-1-oxoethyl)phenyl]carbamate;
N-[5-nitro-2-[2,2,2-trifluoro-1-oxoethyl)phenyl]benzenepropanamide;
N-[4-fluoro-2-(2,2,2-trifluoro-1-oxoethyl)phenyl]furan-2-carboxamide;
N-[2-(2,2,2-trifluoro-1-oxoethyl)phenyl]-1-benzothiophene-2-carboxamide;
α,α,α-trifluoro-N-[2-(2,2,2-trifluoro-1-oxoethyl)phenyl]acetamide;
N-[2-(2,2,2-trifluoro-1-oxoethyl)phenyl]pyridine-2-carboxamide;
N-[2-(2,2,2-trifluoro-1-oxoethyl)phenyl]2-methoxybenzamide;
N-[4-iodo-2-(2,2,2-trifluoro-1-oxoethyl)phenyl]furan-2-carboxamide;
N-[2-(2,2,2-trifluoro-1-oxoethyl)phenyl]4-chlorophenoxyacetamide;
N-[2-(2,2,2-trifluoro-1-oxoethyl)phenyl]indolyl-2-carboxamide;
N-[2-(2,2,2-trifluoro-1-oxoethyl)phenyl]benzofuranyl-2-carboxamide; and
N-[2-(3-(2-propylamino)-3-oxo-2,2-difluoro-1-oxopropyl)phenyl]2-methoxyphenylcarboxamide.

As illustrated, the interconverting tautomers of Formula I (I and I') are encompassed within the scope of the present invention

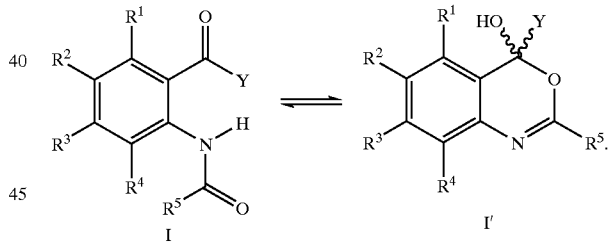

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylthio", "alkoxyalkyl", and "aralkyl" the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "fluoroalkyl" embraces radicals wherein any one or more of the alkyl carbon atoms is substituted with fluoro atoms. Specifically embraced are monohaloalkyl, dihaloalkyl and polyhaloalkyl radicals. A monohaloalkyl radical, for one example, may have either a fluoro atom within the radical. Dihalo and polyhaloalkyl radicals may have two or more fluoro atoms. "Lower fluoroalkyl" embraces radicals having 1–6 carbon atoms. Examples of fluoroalkyl radicals include fluoromethyl, difluoromethyl, trifluoromethyl, pentafluoroethyl, heptafluoropropyl, 1,1-difluoroethyl, and 1,1-difluoropropyl. The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, aralkyl, alkoxy, aryloxy, alkylthio, arylthio, acylamino, peptidyl, amino, halo, nitro, alkoxycarbonyl and aralkoxycarbonyl. The terms "heterocyclyl" or "heterocyclic" embrace saturated, partially saturated and unsaturated heteroatom-containing ring-shaped radicals, where the heteroatoms may be selected from nitrogen, sulfur and oxygen. Examples of saturated heterocyclic radicals include saturated 5 to 7-membered heteromonocylic group containing 1 to 4 nitrogen atoms [e.g. pyrrolidinyl, imidazolidinyl, piperidinyl, piperazinyl, tropanyl, homotropanyl, etc.]; saturated 5 to 7-membered heteromonocyclic group containing 1 to 2 oxygen atoms and 1 to 3 nitrogen atoms [e.g. morpholinyl, etc.]; saturated 5 to 7-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, oxazolinyl, pyrrolinyl, dihydrofuran and dihydrothiazole. Examples of unsaturated heterocyclic radicals, also termed "heteroaryl" radicals include unsaturated 5 to 7 membered heteromonocyclic group containing 1 to 4 nitrogen atoms, for example, pyrrolyl, imidazolyl, pyrazolyl, pyridyl, pyrimidyl, azepinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, furyl, etc.; unsaturated 5 to 7-membered heteromonocyclic group containing a sulfur atom, for example, thienyl, etc.; unsaturated 5 to 7-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 7-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term heteroaryl also embraces radicals where heterocyclic radicals are fused with aryl radicals. Examples of such fused bicyclic radicals include benzofuryl, benzothienyl, and the like. Said "heterocyclyl" radicals may also be substituted at a substitutable position with one or more substituents selected independently from alkyl, aralkyl, alkoxy, aryloxy, alkylthio, arylthio, acylamino, peptidyl, amino, halo, nitro, alkoxycarbonyl and aralkoxycarbonyl. More preferred heteroaryl radicals include five to six membered heteroaryl radicals. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "arylthio" embraces radicals containing an aryl radical, of six to about ten carbon atoms attached to a divalent sulfur atom. Examples of such arylthio radicals are phenylthio, and naphthylthio. The term "aralkylthio" embraces radicals containing an aralkyl radical attached to a divalent sulfur atom. More preferred aralkylthio radicals are "lower aralkylthio" radicals having alkyl radicals of one to six carbon atoms. Examples of such lower aralkylthio radicals are benzylthio and phenylethylthio. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The terms "sulfamyl", "aminosulfonyl" and "sulfonamidyl" denotes $NH_2O_2S$—. The term "acyl" denotes a radical provided by the residue after removal of hydroxyl from an organic acid. Examples of such acyl radicals include formyl, alkanoyl and aroyl radicals. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. "Alkylsulfonyloxy" embraces alkylsulfonyl radicals attached to an oxygen atom, where alkylsulfonyl is defined above. More preferred alkylsulfonyloxy radicals are "lower alkylsulfonyloxy" radicals having one to six carbon atoms. Examples of such lower alkylsulfonyloxy radicals include methylsulfonyloxy, and ethylsulfonyloxy. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted as described above. The terms benzyl and phenylmethyl are interchangeable. The term "aralkoxycarbonyl" means a radical containing an aralkoxy radical, as defined below, attached via an oxygen atom to a carbonyl radical. Preferably, "lower aralkoxycarbonyl" embraces alkoxy radicals having one to six carbon atoms. Examples of such "lower aralkoxycarbonyl" ester radicals include substituted or unsubstituted benzyloxycarbonyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The term "heterocyclylalkyl" embraces heterocyclyl-substituted alkyl radicals. More preferred heterocyclylalkyl radicals are "lower heterocyclylalkyl" radicals having five to ten membered heterocyclyl radicals attached to lower alkyl radicals having one to six carbon atoms. Examples of such radicals include oxazolylmethyl, oxazolylethyl, imidazolylmethyl, imidazolylethyl, oxazolinylmethyl, oxazolinylethyl, indolylethyl, indolylmethyl, pyridylmethyl, thienylmethyl, and furylethyl. The heteroaryl in said heteroaralkyl may be additionally substituted as described above. The term "aryloxy" embraces aryl radicals, as defined above, attached to an oxygen atom. The aryl in said aryloxy may be additionally substituted as described above. Examples of such radicals include phenoxy. The terms "aralkyloxy" and "aralkoxy" embrace oxy-containing aralkyl radicals attached through an oxygen atom to other radicals. More preferred aralkyloxy radicals are "lower aralkoxy" radicals having phenyl radicals attached alkoxy radicals having one to six carbon atoms. Examples include benzyloxy and phenylethoxy. The "aralkoxy" radicals may be further substituted on the aryl ring portion of the radical. The term "aryloxyalkyl" embraces alkyl radicals having one or more aryloxy radicals attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl and phenoxypropyl. The term "alkylamino" denotes amino groups which have been substituted with one or two alkyl radicals. More preferred alkylamino radicals are "lower alkylamino" having alkyl radicals of one to six carbon atoms attached to the nitrogen atom of an amine. Suitable "lower alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups which have been substituted with one or two aralkyl radicals, such as N-benzylamino. The "aralkylamino" radicals may be further substituted on the aryl ring portion of the radical. The term "acylamino" denotes amino groups which have been substituted, through the carbonyl carbon, with one or two acyl radicals. Suitable "acylamino" may be mono or diacylamino such as N-formylamino, N-acetylamino, or the like. The term "(haloalkylcarbonyl)amino" denotes amino groups which have been substituted, through the carbonyl carbon, with one or two haloalkylcarbonyl radicals, as defined above. Suitable "(haloalkylcarbonyl)amino" may be mono (haloalkylcarbonyl)amino such as N-trifluoromethylcarbonylamino, or the like. "Amino acid residue" means any of the naturally occurring alpha-, beta- and gamma-amino carboxylic acids, including their D and L optical isomers and racemic mixtures thereof, synthetic amino acids, and derivatives of these natural and synthetic amino acids. The amino acid residue is bonded either through an amino or an acid functional group of the amino acid. The naturally occurring amino acids which can be incorporated in the present invention include, but are not limited to, alanine, arginine, asparagine, aspartic acid, cysteine, glutamic acid, glutamine, glycine, histidine, isoleucine, leucine, lysine, methionine, ornithine, phenylalanine, proline, serine, threonine, cyclohexylalanine, tryptophan, tyrosine, valine, β-alanine, and γ-aminobutyric acid. Derivatives of amino acids which can be incorporated in the present invention include, but are not limited to amino acids having protected and modified carboxylic acids, including acid esters and amides, protected amines, and substituted phenyl rings, including but not limited to alkyl, alkoxy and halo substituted tyrosine and phenylalanine. The term "peptidyl" denotes a radical having two or three naturally occurring amino acids residues attached together through amide linkages. When the amino acid residue or peptidyl radical is attached from its N-amino terminus, such residues are noted as N-amino acid residue and N-peptidyl, respectively.

The present invention comprises a pharmaceutical composition comprising a therapeutically-effective amount of a compound of Formula I in association with at least one pharmaceutically-acceptable carrier, adjuvant or diluent.

The present invention also comprises a method of therapeutic and prophylactic treatment of a herpesvirus infection, in a subject, the method comprising administering to the subject having such herpes infection a therapeutically-effective amount of a compound of Formula I.

Also included in the family of compounds of Formula I are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized from commercially available starting materials, according to the following procedures of Schemes I–IX, wherein the $R^1$–$R^9$ substituents are as defined for Formulas I–II, above, except where further noted.

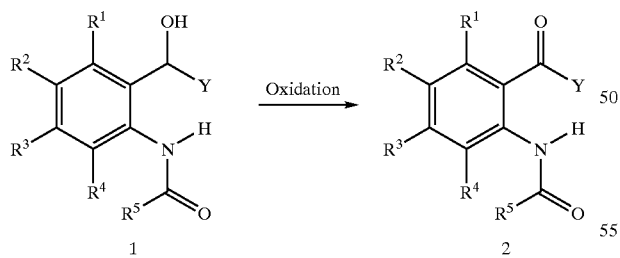

The antiviral agents of this invention can be prepared following the method shown in Scheme I. The antiviral agents 2 are obtained by oxidation of the corresponding alcohol 1, such as by treatment with periodinane (Dess Martin Reagent) [D. Dess and J. Martin, *J. Amer. Chem. Soc.*, 113, 7277 (1991)], or with a modified Pfitzner-Moffatt reagent (DMSO/DCC) (A. Doherty, et al., *J. Med. Chem.*, 35, 2 (1992)].

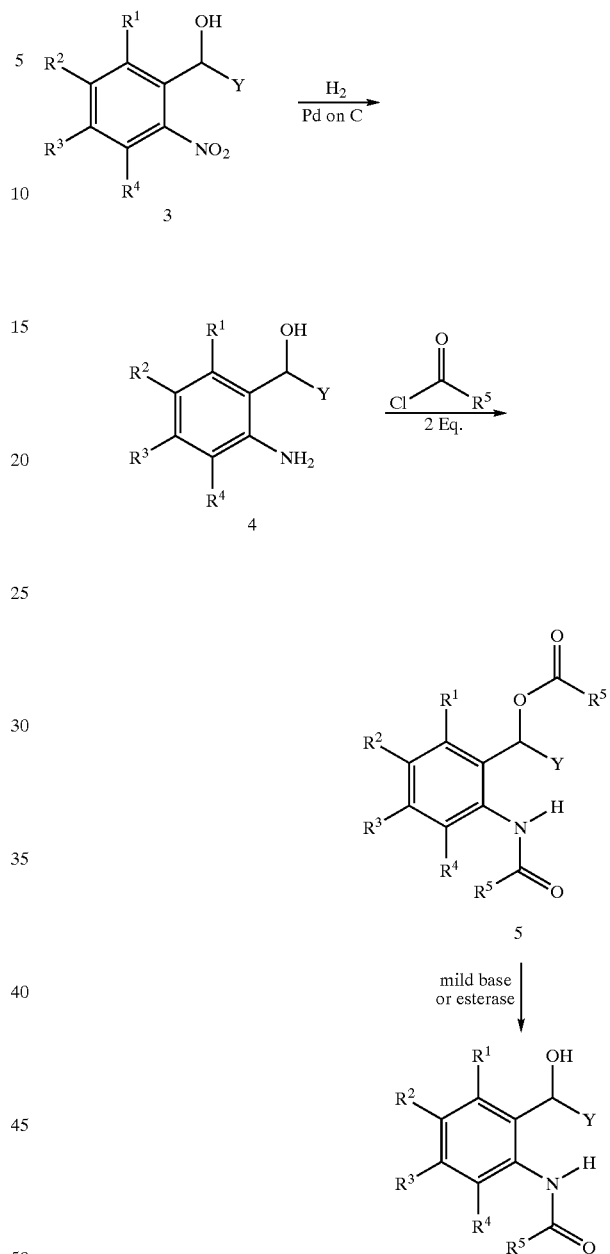

The alcohol 1 can be obtained as outlined in Scheme II. The ortho nitroarylcarbinol 3 can be reduced to the corresponding aniline derivative 4 by catalytic hydrogenation, such as by using palladium on carbon [Rylander, *Hydrogenation Methods,* Chap. 8, (1985)] or alternative methods (stannous chloride reduction or with the anionic hydride [HFe(CO)$_4$]—]. See P. Gaus et al., *Tetrahedron Letters*, 29, 5083 (1988). The aniline carbinol derivative 4 can be diacylated with the appropriate acid chloride in high yield. The resulting ester amide 5 can be selectively cleaved at the ester moiety such as by (1) mild base treatment (e.g. hydroxide ion) which affords the alcohol 1, or by (2) an appropriate esterase.

Scheme III

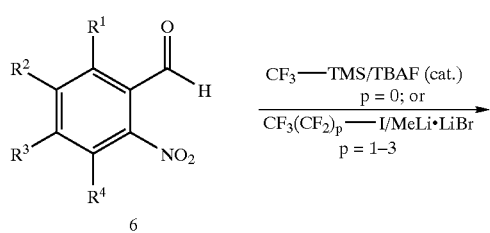

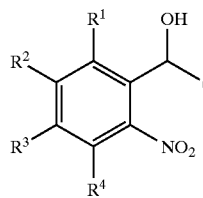

The ortho-nitroarylcarbinol 7 can be obtained, when Y=CF$_3$ (p=0), by treatment of the corresponding aldehyde 6 with trifluoromethyltrimethylsilane (CF$_3$-TMS) and catalytic tetrabutyl ammonium fluoride (TBAF) [Olah et al., *J. Amer. Chem. Soc.*, 111, 393 (1989)]. Alternatively, homologous perfluoroalkyl anions (p=1–3), may be generated by using the appropriate fluoroiodoalkane and an organolithium under transmetaling conditions [J. Begue and D. Delpon, *Tetrahedron*, 47, 3207 (1991)].

Scheme IV

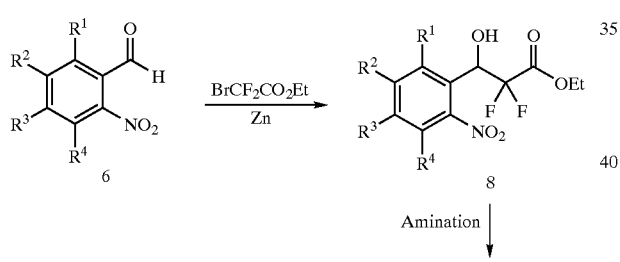

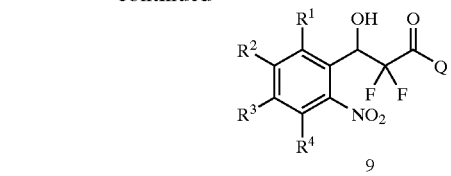

The ortho-nitroarylcarbinol 9 can be obtained, when Y is a difluoroacetamido group, as outlined in Scheme IV. The corresponding aldehyde 6 can be reacted with a Reformatsky reagent prepared from an α-bromo-α,α-difluoroacetylester [Fried et al., *J. Amer. Chem. Soc.*, 114, 8464 (1992); Thaisrivongs et al., *J. Med. Chem.*, 29, 2080 (1986)] to form ester 8. The ester 8 can be reacted directly with primary amines [H$_2$NR$^7$] to afford secondary amides 9 by heating in an appropriate solvent, such as DMF or THF.

Scheme V

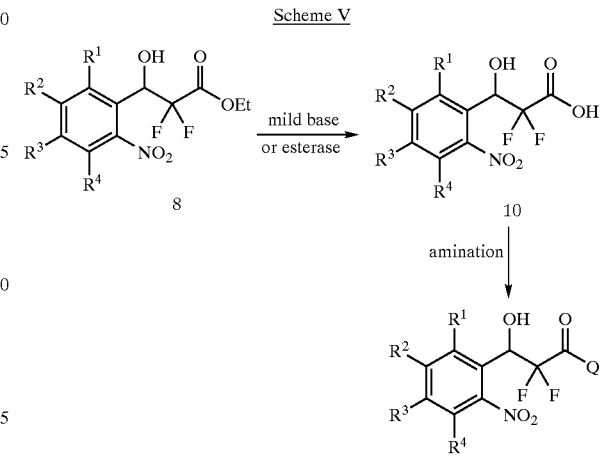

Alternatively, the ester 8 can be cleaved to the free acid 10 and coupled to a primary amine, such as H$_2$NR$^7$, amino acid residue or a peptide, using standard amino acid coupling conditions, for example DSC, DCC, EDC, or BOP, to form compound 9. See Bodansky, *Principles of Peptide Synthesis*, 1984.

Scheme VI

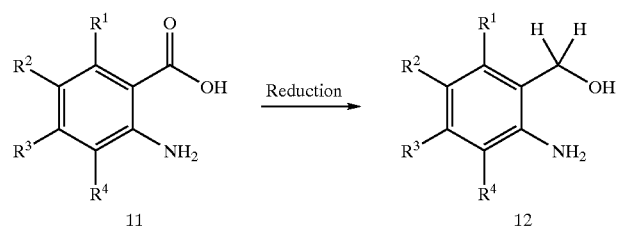

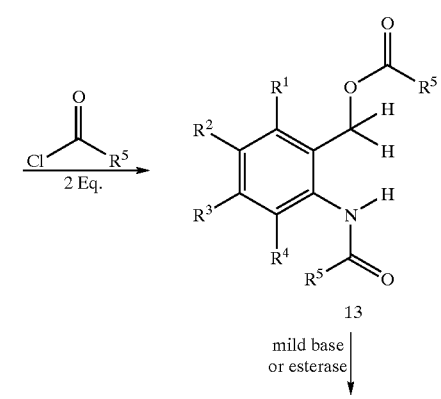

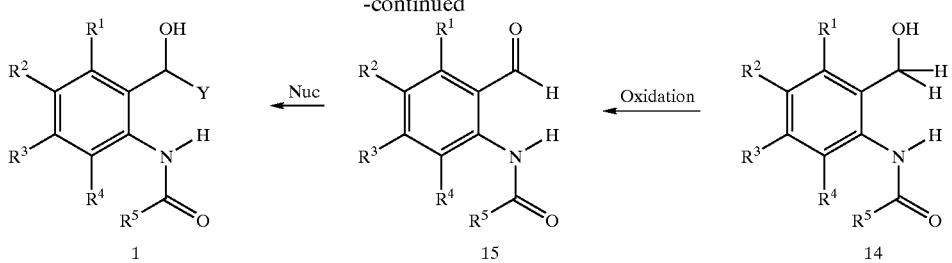

An alternative sequence starts with a commercially available anthranilic acid 11 as outlined in Scheme VI. The carboxylic acid 11 is reduced to the benzyl alcohol 12, such as with borane/THF reagent [Brown and Korytnyk, *J. Amer. Chem. Soc.*, 82, 3866 (1960)]. The benzyl alcohol 12 is diacylated to afford 13. Subsequent selective ester cleavage [see Scheme II] gives the alcohol 14. The alcohol 14 can be oxidized to the aldehyde 15 by known methods (e.g. Swern oxidation—oxalyl chloride, DMSO, triethylamine; or sulfur trioxide/pyridine). The aldehyde 15 can be reacted with nucleophiles (as shown in Scheme III or Scheme IV) to afford carbinol 1.

Several specific examples of antiviral agents obtained through the application of Schemes I–VI are illustrated in Schemes VII–IX. The antiviral agent compound 21 (Example 1) is obtained in five steps starting from ortho nitrobenzaldehyde 16 as shown in Scheme VII. The aldehyde 16 is reacted with $TF_3$-TMS/TBAF to afford carbinol 17. Reduction of the nitro group gives the aniline 18. Bis-acylation of the anilinocarbinol derivative 18 is accomplished by treatment with two equivalents of 2-furoyl chloride to afford ester 19. The ester 19 is cleaved selectively over the amide by treatment with one equivalent of sodium hydroxide at room temperature to afford compound 20. The carbinol 20 is oxidized by treatment with periodinane to afford compound 21.

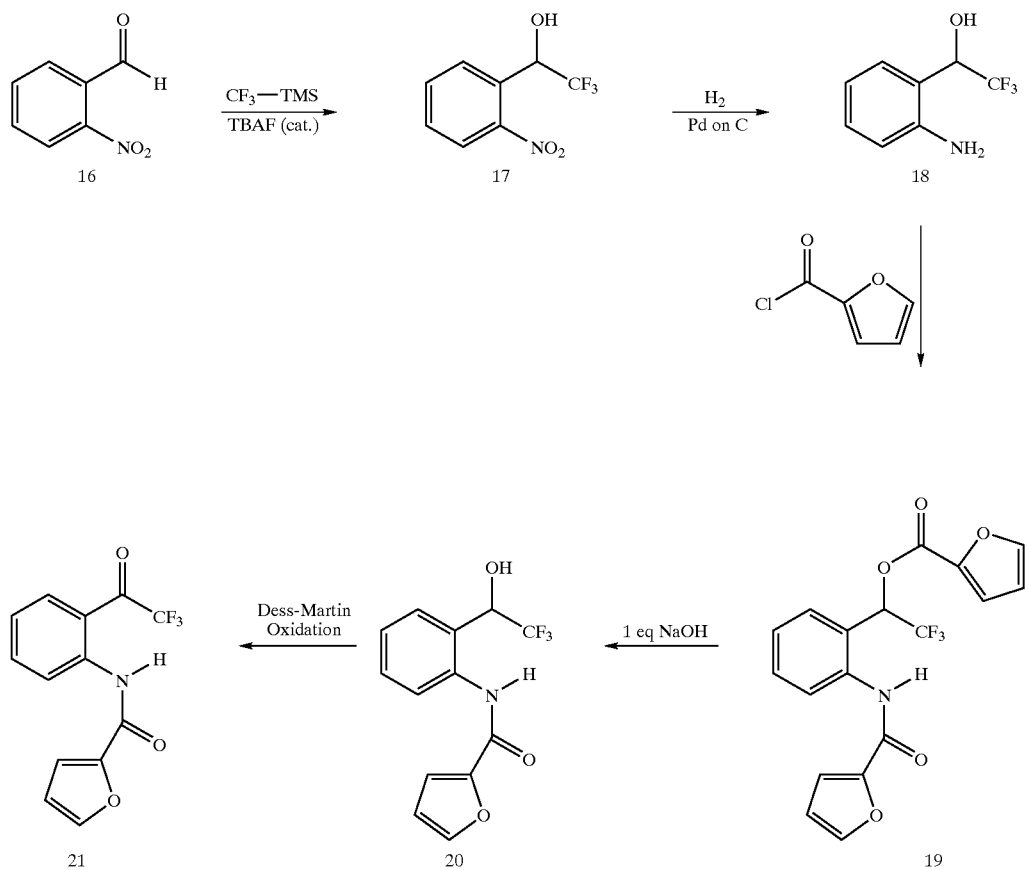

Scheme VIII

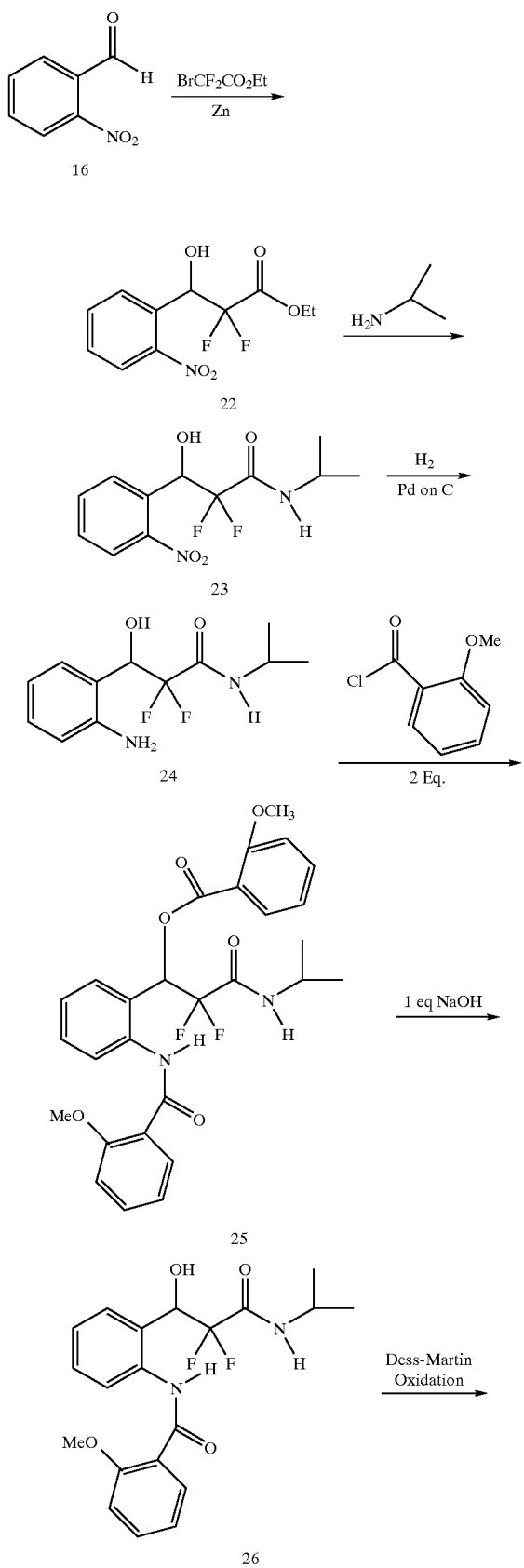

The antiviral agent compound 27 (Example 17) is obtained in six steps from ortho nitrobenzaldehyde 16 as outlined in Scheme VIII. In the first step, carbinol 22 is obtained through a Reformatsky reaction using ethyl bromodifluoroacetate and zinc. In the second step, amidolysis of the ethyl ester of 22 is accomplished by heating compound 22 in the presence of excess isopropylamine in THF to afford compound 23. The ortho-nitro group of compound 23 is reduced by hydrogenation to give the aniline 24. Diacylation of 24 with o-anisolyl chloride affords compound 25. The ester of compound 25 is selectively cleaved by treatment with one equivalent of sodium hydroxide to afford carbinol 26 which is oxidized by periodinane (Dess-Martin reagent) treatment to afford compound 27.

Scheme IX

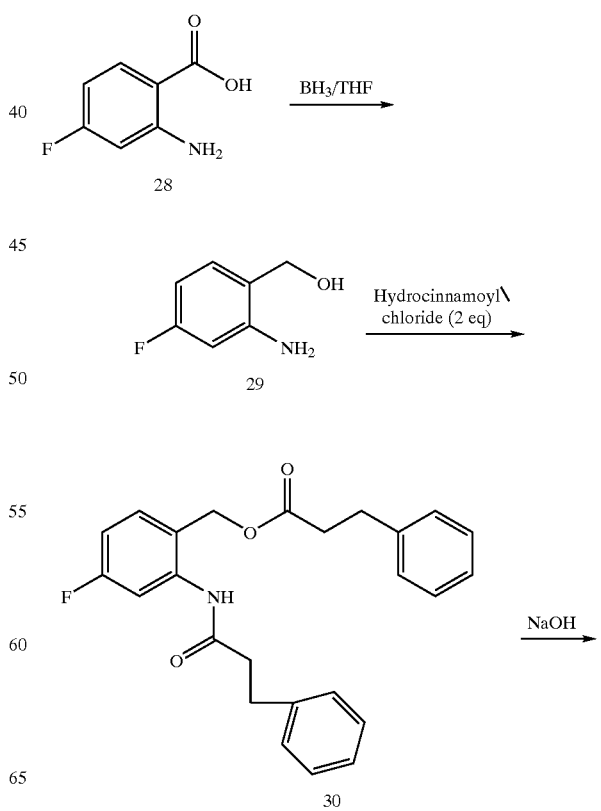

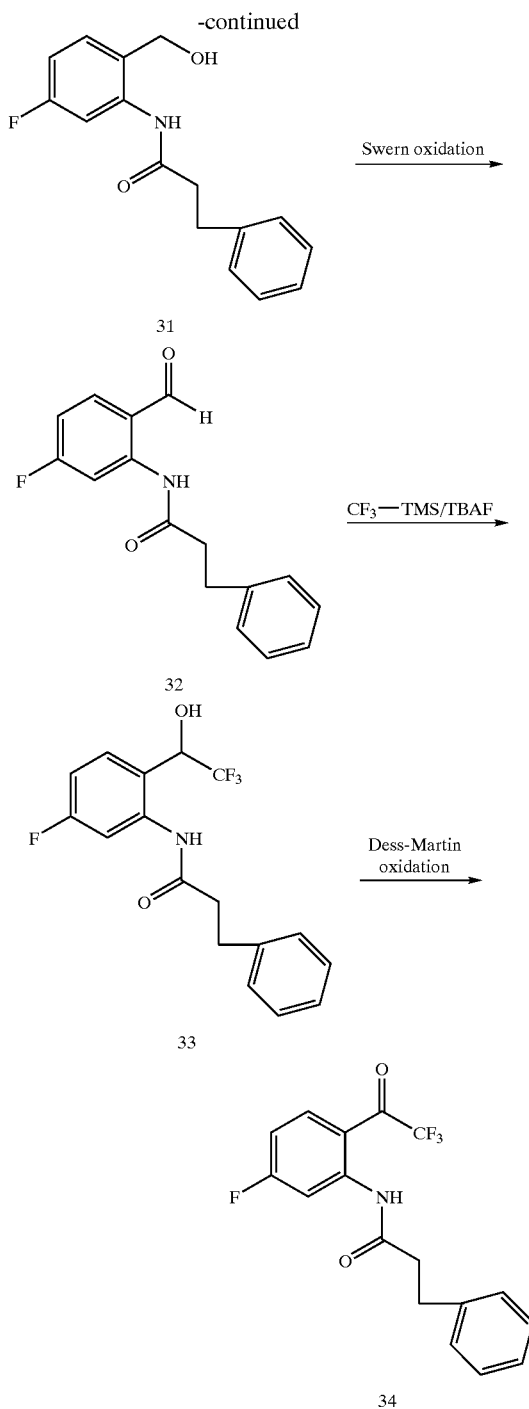

The antiviral agent compound 34 (Example 2) is obtained in six steps from 4-fluoro-2-aminobenzoic acid 28 as outlined in Scheme IX. In the first step, the benzoic acid 28 is reduced to the benzyl alcohol 29 by treatment with borane-THF. Compound 29 is diacylated with hydrocinnamoyl chloride to afford ester 30 which is selectively cleaved at the ester by treatment with one equivalent of sodium hydroxide at room temperature to afford compound 31. The benzyl alcohol of 31 is converted to the benzaldehyde 32 by Swern oxidation. Treatment of 32 with $TF_3$-TMS/TBAF affords carbinol 33. Carbinol 33 is oxidized to ketone 34 by treatment with periodinane (Dess-Martin oxidation).

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

The following abbreviations are used:
EtOAc—ethyl acetate
HCl—hydrochloric acid
DMSO—dimethylsulfoxide
$CDCl_3$—deuterated chloroform
$CHCl_3$—chloroform
$Et_2O$—diethyl ether
$MgSO_4$—magnesium sulfate
$NaHCO_3$—sodium bicarbonate
$KHSO_4$—potassium hydrogen sulfate
$Na_2SO_4$—sodium sulfate
$Na_2S_2O_4$—sodium thiosulfate
DMF—dimethylformamide
NaOH—sodium hydroxide
Pd/C—palladium on carbon
DCC—dicyclohexylcarbodiimide
DSC—disuccinimidylcarbonate
BOP—benzotriazol-1-yloxy-tris(dimethylamino) phosphonium hexafluorophosphate
EDC—1-(3-dimethylaminopropyl)-3-ethylcarbodiimide.HCl
BOC—tert-butyloxycarbonyl
MeOH—methanol
EtOH—ethanol
$CH_2Cl_2$—methylene chloride
h—hour
min—minutes
THF—tetrahydrofuran
IR—infrared
MS—mass spectrum

EXAMPLE 1

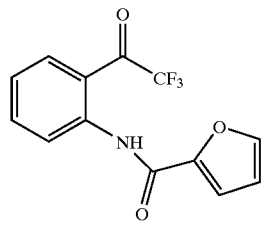

N-[2-(2,2,2-Trifluoro-1-oxoethyl)phenyl]furan-2-carboxamide

Step 1: Preparation of 1,1-trifluoro-2-hydroxy-2-(2-nitrophenyl)ethane

To a mixture of 2-nitrobenzaldehyde (4.25 g, 28.12 mmol) and tetrahydrofuran (75 mL) under argon at 0° C. was added trifluoromethylsilane (5.00 mL), followed by tetrabutylamonium fluoride (1M solution in THF, 75 mL), and the reaction was warmed to 23° C. After 2 h at 23° C., the reaction was treated with 3N HCl (125 mL). After 4 h, the reaction was diluted with ether (75 mL), washed with brine (2×100 mL), and dried ($MgSO_4$). Concentration in vacuo afforded a brown oil (5.45 g, 87.6%) which was taken on to the next step without further purification: $^1$H NMR (CDCl$_3$) δ6.18 (q, J=6 Hz), 7.56 (dd, J=6 Hz, 6 Hz), 7.75 (dd, J=6 Hz, 6 Hz), 7.97 (d, J=6 Hz), 8.05 (d, J=6 Hz); $^{13}$C NMR (CDCl$_3$) 66.6 (q, J=33 Hz), 121.9, 124.9, 127.2 (q, J=280 Hz), 129.3, 130.1, 133.6. IR (neat) 3550–3300 cm$^{-1}$. Anal. Calc'd. for C$_8$H$_6$NO$_3$F$_3$: C, 43.45; H, 2.73; N, 6.33. Found: C, 43.05; H, 2.49; N, 6.02.

Step 2: Preparation of 1,1,1-trifluoro-2-hydroxy-2-(2-aminophenyl)ethane

A solution of 1,1,1-trifluoro-2-hydroxy-2-(2-nitrophenyl)ethane from Step 1 (5.45 g, 24.64 mmol) in 90 mL of ethanol was hydrogenated over 200 mg of Raney Nickel at 5 psi hydrogen over a 8 h period at 23° C. After removing the catalyst by filtration, concentration in vacuo afforded a quantitative yield of 1,1,1-trifluoro-2-hydroxy-2-(2-aminophenyl)ethane as a orange-yellow solid: $^1$H NMR (CDCl$_3$) δ4.32 (br s), 5.03 (q, J=6 Hz), 6.28 (br s), 6.67–6.78 (m), 7.08–7.23 (m); $^{13}$C NMR (CDCl$_3$) 66.6 (q, J=33 Hz), 121.9, 124.9, 127.2 (q, J=280 Hz,), 129.3, 130.1, 133.6; MS (EI) 191 (M$^+$), 173, 122. IR (neat) 3395, 3325, 3400–3100. Anal. Calc'd. for C$_8$H$_8$NOF$_3$: C, 50.26; H, 4.22; N, 7.33. Found: C, 50.47; H, 4.57; N, 7.05.

Step 3: Preparation of N-[2-(2,2,2-trifluoro-1-hydroxyethyl)phenyl]furan-2-carboxamide To a solution of 1,1,1-trifluoro-2-hydroxy-2-(2-aminophenyl)ethane from Step 2 (600 mg, 3.14 mmol), methylene chloride (10 mL) was added N,N,-diisopropylethylamine (893 mg, 6.91 mmol) followed by 2-furoyl chloride (902 mg, 6.91 mmol) dropwise over 5 min under an argon atmosphere at 23° C. After 18 h, the reaction was diluted with ether (100 mL), washed with KHSO$_4$ (1N, 1×80 mL), sat'd NaHCO$_3$ (1×80 mL), brine (1×80 mL) and dried (MgSO$_4$). After concentration in vacuo, the crude residue was taken on to the next step. The residue was dissolved in ethyl acetate (300 mL), washed with KHSO$_4$ (2×50 mL) and with brine (1×50 mL), dried (Na$_2$SO$_4$), and concentrated in vacuo. To a solution of the residue and methanol (3 mL) was added NaOH (1.5 N, 3 mL) at 23° C. under argon. After 2 h at 23° C., the reaction was concentrated in vacuo, diluted with ether (150 mL), washed with brine (100 mL) and dried (MgSO$_4$). After concentration in vacuo, the residue was purified by flash chromatography (ethyl acetate:hexane 1:3) to afford N-[2-(2,2,2-trifluoro-1-hydroxyethyl)phenyl]furan-2-carboxamide (717 mg, 80%) as an oil: $^1$H NMR (CDCl$_3$) δ5.14 (q, J=6 Hz), 6.55 (m), 7.16–7.58 (m), 8.25 (m); $^{13}$C NMR (CDCl$_3$) 72.7 (q, J=33 Hz), 112.2, 115.0, 122.7,123.1, 126.5 (q, J=280 Hz), 129.7, 136.8, 144.7, 149.5, 169.6. MS (EI) 285 (M$^+$), 245, 216. IR (neat) 3500–3000, 1650 cm$^{-1}$. Anal. Calc'd. for C$_{13}$H$_{10}$NO$_3$F$_3$: C, 54.74; H, 3.53; N, 4.91. Found: C, 54.63; H, 3.50; N, 4.90.

Step 4: Preparation of N-[2-(2,2,2-trifluoro-1-oxoethyl)phenyl]furan-2-carboxamide To a solution of N-[2-(2,2,2-trifluoro-1-hydroxyethyl)phenyl]furan-2-carboxamide from Step 3 (336 mg, 1.18 mmol) and methylene chloride (31 mL) was added 1,1,1-triacetoxy-1,1-dihydro-1,2-benziodoxyl-3(1H)-one (2.00 g, 4.72 mmol), followed by tert-butanol (3.1 mL) under an argon atmosphere at 23° C. After 18 h, sat'd NaHCO$_3$ (31 mL) was added followed by solid sodium thiosulfate (5.20 g, 32.9 mmol). After 1 h at 23° C., the organic layer was separated from the aqueous. The aqueous layer was extracted with ether (2×100 mL), and the combined organics were washed with sat'd NaHCO$_3$:sat'd Na$_2$S$_2$O$_3$ (3×80 mL) and brine (1×80 mL), and dried (MgSO$_4$). After concentration in vacuo, the crude residue was purified by flash chromatography (ethyl acetate:hexane 1:3) which afforded (312 mg) as a yellow gum: $^1$H NMR (CDCl$_3$) δ6.60 (m), 7.20–7.35 (m), 7.67 (br s), 7.75 (m), 8.03 (m), 9.01 (d, J=6 Hz), 11.93 (brs); $^{13}$C NMR (CDCl$_3$) 112.5, 114.6, 115.4, 116.1, 118.4, 121.2, 122.4 (q, J=280 Hz), 122.8, 131.8, 131.9,137.6, 143.1, 145.2, 156.7. MS (EI) 283 (M$^+$), 258, 256, 214. IR (neat) 1674 cm$^{-1}$. Anal. Calc'd. for C$_{13}$H$_8$NO$_3$F$_3$: C, 55.13; H, 2.85; N, 4.95. Found: C, 51.01; H, 2.66; N, 4.52.

EXAMPLE 2

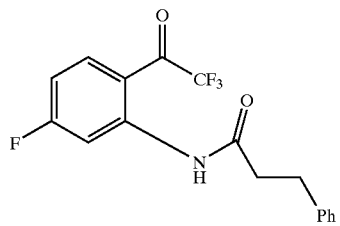

N-[5-Fluoro-2-(2,2,2-trifluoro-1-oxoethyl)phenyl]benzenepropanamide

Step 1: Preparation of 2-amino-4-fluorobenzyl alcohol

To a solution of 2-amino-4-fluorobenzoic acid (3.00 g, 19.3 mmol) and THF (40 mL) at 0° C. under argon, borane-THF complex (1M THF solution, 77.0 mmol) was added dropwise over 30 min. After complete addition, the reaction was warmed to 23° C. After 4 h, the reaction mixture was added slowly (5 min) to ethanol (77 mL). After 20 min, the reaction was concentrated in vacuo, diluted with sat'd NaHCO$_3$ (100 mL), extracted with ethyl acetate (2×100 mL), washed with brine (1×100 mL), and dried (MgSO$_4$). After concentration in vacuo, the residue was purified by passing through a silica gel pad (1:1 ethyl acetate:hexane). Concentration in vacuo afforded 2.02 g of 2-amino-4-fluorobenzyl alcohol as a yellow solid which was sufficiently pure to take on to the next step: $^1$H NMR (CDCl$_3$) δ4.54 (br s), 6.28–6.47 (m), 6.93–7.05 (m); $^{13}$C NMR (CDCl$_3$) δ62.7, 101.9 (J=24 Hz), 103.4 (J=21 Hz), 121.5, 130.1 (J=10 Hz), 149.1, 163 (J=360 Hz). MS (EI) 141 (M$^+$), 124, 110. IR (neat) 3500–3000 cm$^{-1}$.

Step 2: Preparation of N-[5-fluoro-2-hydroxymethylphenyl]benzenepropanamide

To a solution of 2-amino-4-fluorobenzyl alcohol from Step 1 (2.00 g, 14.17 mmol) and methylene chloride (45 mL), was added N,N,-diisopropylethylamine (3.70 g, 28.34 mmol) followed by hydrocinnamoyl chloride (4.78 g, 28.34 mmol) dropwise over 15 min under an argon atmosphere at 23° C. After 16 h, the reaction was diluted with methylene chloride (100 mL), washed with KHSO$_4$ (1 N, 1×80 mL), sat'd NaHCO$_3$ (1×80 mL), brine (1×80 mL) and dried (MgSO$_4$). After concentration in vacuo, the crude residue was dissolved in methanol (14 mL) and NaOH (1.5 N, 14 mL) was added at 23° C. under argon. After 2 h at 23° C., the reaction was concentrated in vacuo, diluted with ether (150 mL), washed with brine (100 mL), and dried (MgSO$_4$). After concentration in vacuo, the residue was purified by flash chromatography (ethyl acetate:hexane 1:3) to afford N-[5-fluoro-2-hydroxymethylphenyl]benzenepropanamide (3.40 g, 87.8%) as an oil: $^1$H NMR (CDCl$_3$) δ2.65 (t, J=7 Hz), 3.05 (t, J=7 Hz), 4.48 (s), 6.68–6.74 (m), 7.00–7.34 (m), 7.83–7.91 (m) 8.72 (br s). MS (EI) 273, 255, 212. IR (neat) 3500–3150, 1667 cm$^{-1}$. Anal. Calc'd. for C$_{16}$H$_{16}$NO$_2$F: C, 70.31; H, 5.90; N, 5.13. Found: C, 70.26; H, 6.11; N, 5.03.

Step 3: Preparation of N-[5-fluoro-2-oxomethylphenyl]benzenepropanamide

To a solution of oxalyl chloride (4.46 g, 35.13 mmol) and methylene chloride (300 mL) at −78° C. was added dimethyl sulfoxide (3.29 g, 42.15 mmol) over 15 min. After 15 min at −78° C., a solution of N-[5-fluoro-2-hydroxymethylphenyl]benzenepropanamide from Step 2 (3.20 g, 11.7 mmol) and methylene chloride (300 mL) was added over 10 min. After 45 min at −78° C., triethylamine (8.53 g, 84.3 mmol) was added and the reaction was warmed to 23° C. After 20 min at 23° C., the reaction was washed with sat'd NaHCO$_3$ (2×100 mL), brine (1×100 mL) and dried (MgSO$_4$). After concentration in vacuo, the crude residue was purified by flash chromatography (ethyl acetate: hexane 1:3) which afforded the aldehyde as an oil (2.71 g, 85.4%): $^1$H NMR (CDCl$_3$) δ2.79 (t, J=7 Hz), 3.06–3.16 (m), 6.85–6.93 (m), 7.17–7.37 (m), 7.63–7.69 (m), 8.52–8.58 (m), 9.84 (s).

Step 4: Preparation of N-[5-fluoro-2-(2,2,2-trifluoro-1-hydroxyethyl)phenyl]benzenepropanamide To a mixture of aldehyde from Step 3 (252 mg, 0.929 mmol) and THF (8 mL) under argon at 0° C., was added trifluoromethylsilane (132 mg, 0.929 mmol), followed by tetrabutylammonium fluoride (1M solution in THF, 50 mL). The reaction was warmed to 23° C. After 2 h at 23° C., the reaction was treated with 3N HCl (125 mL). After 4 h, the reaction was diluted with ether (75 mL), washed with brine (2×100 mL), and dried (MgSO$_4$). Concentration in vacuo afforded a brown oil (214 mg, 67.4%) which was taken on to the next step without further purification: $^1$H NMR (CDCl$_3$) δ2.63 (t, J=7 Hz), 2.97 (t, J=7 Hz), 4.68 (br s), 4.88 (q, J=6 Hz), 6.73–6.82 (m), 7.11–7.35 (m), 7.83–7.92 (m), 8.85 (br s). IR (neat) 3450–3050, 1667 cm$^{-1}$. MS (EI) 341 (M$^+$), 323, 209, 140. Anal. Calc'd. for C$_{17}$H$_{15}$NO$_2$F$_4$: C, 59.82; H, 4.43; N, 4.10. Found: C, 59.81; H, 4.57; N, 4.08.

Step 5: Preparation of N-[5-fluoro-2-(2,2,2-trifluoro-1-oxoethyl)phenyl]benzenepropanamide To a solution of N-[5-fluoro-2-(2,2,2-trifluoro-1-hydroxyethyl)phenyl]benzenepropanamide from Step 4 (178 mg, 0.521 mmol) and methylene chloride (15 mL) was added 1,1,1-triacetoxy-1,1-dihydro-1,2-benziodoxyl-3(1H)-one (885 mg, 2.08 mmol) followed by tert-butanol (15 mL) under an argon atmosphere at 23° C. After 18 h, sat'd NaHCO$_3$ (31 mL) was added followed by solid sodium thiosulfate (5.20 g, 32.9 mmol). After 1 h at 23° C., the organic layer was separated from the aqueous. The aqueous was extracted with ether (2×100 mL), and the combined organics were washed with sat'd NaHCO$_3$:sat'd Na$_2$S$_2$O$_3$ (3×80 mL), brine (1×80 mL), and dried (MgSO$_4$). After concentration in vacuo, the crude residue was purified by flash chromatography (ethyl acetate:hexane 1:3) which afforded N-[5-fluoro-2-(2,2,2-trifluoro-1-oxoethyl)phenyl]benzenepropanamide (80 mg) as a yellow gum: $^1$H NMR (CDCl$_3$) δ2.78 (t, J=7 Hz), 3.07 (t, J=7 Hz), 6.82–6.91 (m), 7.17–7.33 (m), 7.92–8.03 (m), 8.67–8.73 (m), 11.11 (br s); $^{13}$C NMR (CDCl$_3$) δ31.0, 40.2, 108.2 (d, J=27.8 Hz), 110.45 (d, J=22.5 Hz), 111.6, 116.4 (q, J=290 Hz), 126.4, 128.2, 128.5, 134.5 (d, J=5 Hz), 139.9, 139.9, 146.2 (d, J=14 Hz), 167.9 (d, J=258 Hz), 171.6,181.9. MS (EI) 339 (M$^+$), 320, 270, 207. IR (neat) 1712, 1677 cm$^{-1}$. Anal. Calc'd. for C$_{17}$H$_{13}$NO$_2$F$_4$: C, 60.18; H, 3.86; N, 4.13. Found: C, 59.82; H, 4.08; N, 3.94.

EXAMPLE 3

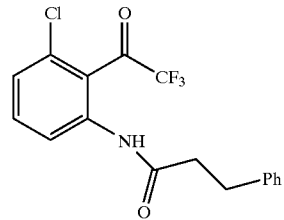

N-[3-Chloro-2-(2,2,2-trifluoro-1-oxoethyl)phenyl]benzenepropanamide

The title compound was prepared in the manner of Example 1, substituting 2-nitro-6-chlorobenzaldehyde for 2-nitrobenzaldehyde in Step 1 and hydrocinnamoyl chloride for furoyl chloride in Step 3. Purification by flash chromatography afforded the title compound as an oil: $^1$H NMR (CDCl$_3$) δ2.64 (t, J=7 Hz), 3.03 (t, J=7 Hz), 7.14–7.68 (m); $^{13}$C NMR (CDCl$_3$) δ31.0, 38.5, 115.4 (q, J=290 Hz), 117.1, 122.6, 126.4, 126.6, 128.2, 128.6, 132.8, 136.1, 139.8. MS (EI) 355 (M$^+$), 286, 258, 223. IR (neat) 1734, 1662 cm$^{-1}$. Anal. Calc'd. for C$_{17}$H$_{13}$NO$_2$F$_3$Cl: C, 57.39; H, 3.68; N, 3.94; Cl, 9.97. Found: C, 57.07; H, 3.79; N, 3.83; Cl, 9.21.

EXAMPLE 4

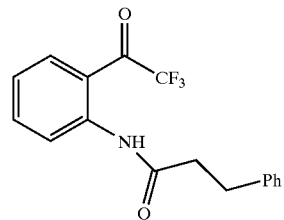

N-[2-(2,2,2-Trifluoro-1-oxoethyl)phenyl]benzenepropanamide

The title compound was prepared in the manner of Example 1 substituting 2-nitro-6-chlorobenzaldehyde for 2-nitrobenzaldehyde in Step 1 and hydrocinnamoyl chloride for furoyl chloride in Step 3. Purification by flash chromatography afforded the title compound as an oil: $^1$H NMR (CDCl$_3$) δ2.78 (t, J=7 Hz), 3.09 (t, J=7 Hz), 7.14–7.35 (m), 7.71 (m), 7.96 (br d, J=7 Hz), 8.84 (d, J=7 Hz); $^{13}$C NMR (CDCl$_3$) δ31.2, 40.2, 115.1, 117.1 (q, J=290 Hz), 121.2, 122.6, 126.3, 128.2, 128.5, 131.6, 131.7, 137.6, 140.1, 143.3, 171.4, 181.4 (q, J=63 Hz). MS (EI) 321 (M$^+$), 252, 189. IR (neat) 3346, 1682 cm$^{-1}$. Anal. Calc'd. for C$_{17}$H$_{13}$NO$_2$F$_3$Cl: C, 63.55; H, 4.39; N, 4.36. Found: C, 63.36; H, 4.34; N, 4.16.

EXAMPLE 5

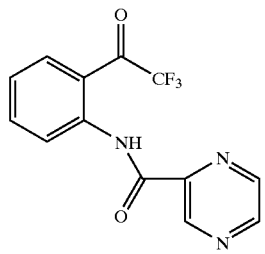

N-[2-(2,2,2-Trifluoro-1-oxoethyl)phenyl]pyrazine-2-carboxamide

The title compound was prepared in the manner of Example 1, substituting pyrazine-2-carbonyl chloride for furoyl chloride in Step 3. Purification by flash chromatography afforded the title compound as an oil: $^1$H NMR (CDCl$_3$) δ7.30 (td, J=8, 1 Hz), 7.80 (td, J=8, 1 Hz), 8.06 (dp, J=8,1 Hz), 8.77 (dd, J=2,1 Hz), 8.85 (d, J=2 Hz), 9.07 (dd, J=8,1 Hz), 9.51 (d, J=1 Hz); $^{13}$C NMR (CDCl$_3$) δ116.4, 116.4 (q, J=290 Hz), 121.5, 123.4, 131.9, 137.4, 142.1, 142.9, 144.4, 144.8, 147.7, 162.4. MS (EI) 295 (M$^+$), 226, 198. IR (neat) 3244, 1689 cm$^{-1}$.

EXAMPLE 6

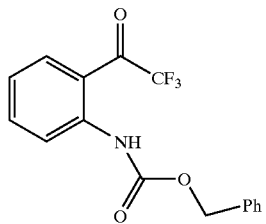

Phenylmethyl N-[2-(2,2,2-trifluoro-1-oxoethyl)phenyl]carbamate

The title compound was prepared in the manner of Example 1, substituting benzylchloroformate for furoyl chloride in Step 3. Purification by flash chromatography afforded the title compound as an oil: $^1$H NMR (CDCl$_3$) δ5.24 (s), 7.05–7.96 (m), 8.61 (d, J=8 Hz); $^{13}$C NMR (CDCl$_3$) δ67.3, 114.8, 117.3 (q, J=290 Hz), 119.6, 121.8, 128.2, 128.3, 131.6, 135.6, 137.4, 143.8, 153.1, 182.2 (q, J=53 Hz). MS (EI) 323 (M$^+$), 298, 91. IR (neat) 3312, 1741, 1682 cm$^{-1}$. Anal. Calc'd. for C$_{16}$H$_{12}$NO$_3$F$_3$: C, 59.44; H, 3.74; N, 4.33. Found: C, 58.75; H, 3.66; N, 4.22.

EXAMPLE 7

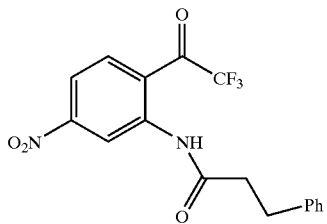

N-[5-Nitro-2-[2,2,2-trifluoro-1-oxoethyl)phenyl]benzenepropanamide

The title compound was prepared in the manner of Example 2, substituting 2-amino-4-nitrobenzoic acid for 2-amino-4-fluorobenzoic acid in Step 1. Purification by flash chromatography afforded the title compound as an oil: $^1$H NMR (4:1 mixture of tautomers, CDCl$_3$) δ2.64 (t, J=7 Hz), 2.73 (t, J=7 Hz), 2.94 (t, J=7 Hz), 3.07 (t, J=7 Hz), 6.50 (br s), 7.14–7.33 (m), 7.71–8.14 (m), 9.14 (br d, J=1 Hz), 9.56 (br d, J=1 Hz), 10.72 (br s); $^{13}$C NMR (CDCl$_3$) δ31.8 (minor), 32.0 (major), 40.5 (minor), 41.0 (major), 117.0, 117.2, 117.5 (q, J=290 Hz), 117.7, 117.8, 127.4, 129.1, 129.2, 129.5, 129.6, 131.4, 132.7, 133.6, 139.2, 140.7, 144.6, 149.8, 153.0, 172.9, 183.8 (q, J=63 Hz).

EXAMPLE 8

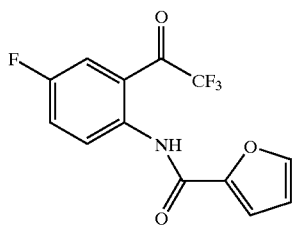

N-[4-Fluoro-2-(2,2,2-trifluoro-1-oxoethyl)phenyl]furan-2-carboxamide

The title compound was prepared in the manner of Example 2 substituting 2-furoyl chloride for hydrocinnamoyl chloride in Step 2. The crude residue was purified by flash chromatography (ethyl acetate:hexane 1:3) to afford the title compound: $^1$H NMR (CDCl$_3$) δ6.61 (dd, J=3,2 Hz), 6.93 (ddd, J=9,8,2.5 Hz), 7.34 (dd, J=3,1 Hz), 7.66 (dd, J=2,1 Hz), 8.06 (ddq, J=8, 7, 2), 8.82 (dd, J=12.5, 2.5), 12.17 (br s); $^{13}$C NMR (CDCl$_3$) δ108.4 (d, J=28.5 Hz), 110.75 (d, J=22.5 Hz), 112.8, 114.3 (q, J=290 Hz), 116.8, 118.5, 126.4, 134.8 (d, J=3 Hz), 145.6, 146.4 (d, J=5 Hz), 147.3, 156.9, 168.0 (d, J=262 Hz), 181.9 (q, J=63 Hz).

EXAMPLE 9

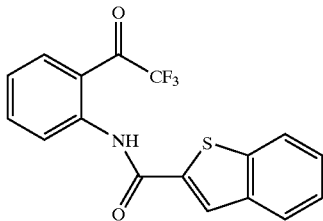

N-[2-(2,2,2-Trifluoro-1-oxoethyl)phenyl]-1-benzothiophene-2-carboxamide

The title compound was prepared in the manner of Example 1, substituting 2-thianapthenenecarbonyl chloride for furoyl chloride in Step 3. Purification by flash chromatography afforded the title compound as an oil: $^1$H NMR (CDCl$_3$) δ7.42 (m), 7.75–7.83 (m), 7.86–7.99 (m), 8.05–8.11 (m), 9.03 (br d). MS (EI) 349 (M$^+$), 280, 248, 161. Anal. Calc'd. for C$_{17}$H$_{10}$NO$_2$F$_3$S plus 1.25 H$_2$O: C, 54.91; H, 3.39; N, 3.77. Found: C, 54.57; H, 3.02; N, 3.21.

EXAMPLE 10

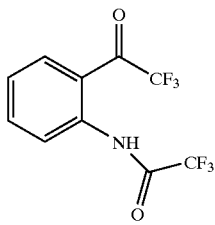

α,α,α-Trifluoro-N-[2-(2,2,2-trifluoro-1-oxoethyl)phenyl]acetamide

The title compound was prepared in the manner of Example 1, substituting trifluoroacetic anhydride for furoyl chloride in Step 3 and $K_2CO_3$ for 1N NaOH in Step 3. Purification by flash chromatography afforded the title compound as an oil: $^1$H NMR (CDCl$_3$) δ7.34–7.44 (m), 7.76–7.83 (m), 8.05–8.12 (m), 8.76 (d).

EXAMPLE 11

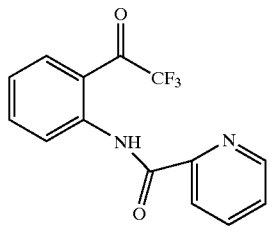

N-[2-(2,2,2-Trifluoro-1-oxoethyl)phenyl]pyridine-2-carboxamide

The title compound was prepared in the manner of Example 1, substituting picolinoyl chloride for furoyl chloride in Step 3. Purification by flash chromatography afforded the title compound as an oil: Anal. Calc'd. for $C_{14}H_9N_2O_2F_3$: C, 57.15; H, 3.08; N, 9.52. Found: C, 56.53; H, 2.93; N, 9.34.

EXAMPLE 12

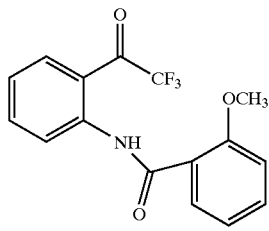

N-[2-(2,2,2-Trifluoro-1-oxoethyl)phenyl]2-methoxybenzamide

The title compound was prepared in the manner of Example 1 substituting 2-methoxybenzoyl chloride for furoyl chloride in Step 3. Purification by flash chromatography afforded the title compound as an oil: MS (EI) 323 (M$^+$). Anal. Calc'd. for $C_{16}H_{12}NO_3F_3$: C, 59.44; H, 3.74; N, 4.33. Found: C, 59.27; H, 3.99; N, 3.66.

EXAMPLE 13

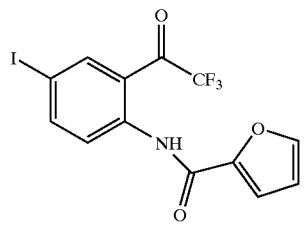

N-[4-Iodo-2-(2,2,2-trifluoro-1-oxoethyl)phenyl]furan-2-carboxamide

The title compound was prepared in the manner of Example 2, substituting 5-iodo-2-aminobenzoic acid for 2-amino-4-fluorobenzoic acid in Step 1 and furoyl chloride for hydrocinnamoyl chloride in Step 2. Purification by flash chromatography afforded the title compound as an oil.

EXAMPLE 14

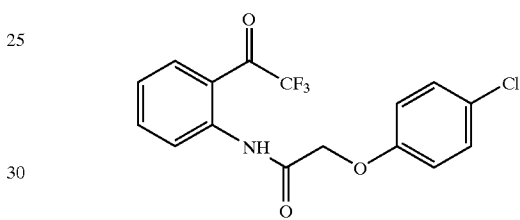

N-[2-(2,2,2-Trifluoro-1-oxoethyl)phenyl]4-chlorophenoxyacetamide

The title compound was prepared in the manner of Example 1, substituting 4-chlorophenoxyacetyl chloride for furoyl chloride in Step 3. Purification by flash chromatography afforded the title compound as a beige solid: mp 134–135° C. MS (EI) 357 (M+), 288, 230, 202. Anal. Calc'd. for $C_{16}H_{11}ClF_3NO_3$: C, 53.72; H, 3.10; N, 3.92. Found: C, 53.80; H, 3.14; N, 3.77.

EXAMPLE 15

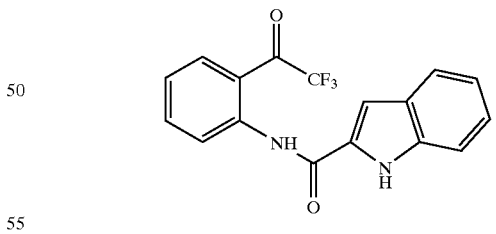

N-[2-(2,2,2-Trifluoro-1-oxoethyl)phenyl]indolyl-2-carboxamide

Step 1: Preparation of indole-2-carbonyl chloride

To a solution of indole-2-carboxylic acid (960 mg, 6.0 mmol), 10 mL $CH_2Cl_2$ and 2 drops DMF under argon at 0° C., was added oxalyl chloride (2.68 mL, 24.0 mmol) dropwise. The reaction was stirred at 23° C. for 3.5 hours and then concentrated in vacuo to yield a yellow oil which was taken on to the next step without further purification.

Step 2: Preparation of N-[2,2,2-trifluoro-1-oxoethyl)phenyl]indolyl-2-carboxamide The title compound was prepared in the manner of Example 1, substituting indole-2-carbonyl chloride from Step 1 for the furoyl chloride in Example 1, Step 3. Purification of the title compound by flash chromatography afforded a yellow solid: mp 188–193° C. MS (EI) 332 (M+), 144. Anal. Calc'd. for $C_{17}H_{11}F_3N_2O_2$ plus 0.35 mol $H_2O$: C, 60.30; H, 3.48; N, 8.27. Found: C, 60.22; H, 3.56; N, 7.83.

EXAMPLE 16

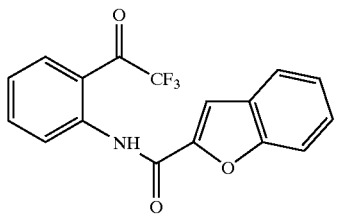

N-[2-(2,2,2-Trifluoro-1-oxoethyl)phenyl] benzofuranyl-2-carboxamide

The title compound was prepared in the manner of Example 1, substituting 2-benzofurancarbonyl chloride for the furoyl chloride in Step 3. The 2-benzofurancarbonyl chloride was prepared in the manner of Example 15; Step 1, substituting 2-benzofurancarboxylic acid for the indole-2-carboxylic acid. Purification of the title compound by flash chromatography afforded a yellow solid: mp 130–132° C. MS (EI) 333 (M+), 264, 145. Anal. Calc'd. for $C_{17}H_{10}F_3NO_3$: C, 61.27; H, 3.02; N, 4.20. Found: C, 60.94; H, 2.76; N, 4.11.

EXAMPLE 17

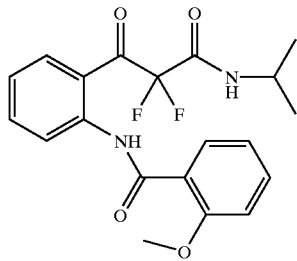

N-[2-(3-(2-Propylamino)-3-oxo-2,2-difluoro-1-oxopropyl)phenyl]2-methoxyphenylcarboxamide Step 1: Preparation of 2-(3-ethoxy-3-oxo-2,2-difluoro-1-hydroxypropyl)nitrobenzene To a slurry of activated zinc (6.25 g, 99.2 mmol) in 75 mL anhydrous THF, was added ethyl bromodifluoroacetate (11.0 mL, 85.8 mmol) and the mixture was heated to reflux. After a visible reaction had occurred, 2-nitrobenzaldehyde (5.0 g, 33.1 mmol) in 30 mL anhydrous THF, was added dropwise to maintain reflux. After 3 h, the solution was cooled to 23° C., diluted with EtOAc (50 mL), washed with 1M $KHSO_4$ (2×50 mL) and brine (1×50 mL), and dried ($Na_2SO_4$). Concentration in vacuo yielded a residue which was purified by flash chromatography (chloroform:EtOH, 99:1) to afford 2-(3-ethoxy-3-oxo-2,2-difluoro-1-hydroxypropyl) nitrobenzene (8.28 g, 91%) as an orange 30 oil, which was taken on to the next step without further characterization.

Step 2: Preparation of 2-(3-(2-propylamino)-3-oxo-2,2-difluoro-1-hydroxypropyl)nitrobenzene To a solution of the ester from Step 1 (1.50 g, 5.45 mmol) in EtOH (20 mL) was added isopropylamine (1.86 mL, 21.8 mmol). The solution was heated to reflux for 20 h and cooled to ambient temperature. Concentration under a nitrogen atmosphere afforded the amide quantitatively: Anal. Calc'd. for $C_{12}H_{14}F_2N_2O_4$ plus 0.15 mol $H_2O$: C, 49.54; H, 4.95; N, 9.63. Found: C, 49.52; H, 5.52; N, 9.46.

Step 3: Preparation of 2-(3-(2-propylamino)-3-oxo-2,2-difluoro-1-hydroxypropyl)aniline A solution of the amide from Step 2 (2.0 g, 7.25 mmol) in 50 mL EtOH was hydrogenated over 4% Pd/C at 5 psi for 1 h at 23° C. After removing the catalyst by filtration, concentration in vacuo afforded a quantitative amount of the amine as a brown oil which was taken on to the next step without further purification.

Step 4: Preparation of N-[2-(3-(2-propylamino)-3-oxo-2,2-difluoro-1-hydroxypropyl)phenyl]-2-methoxyphenylcarboxamide To a solution of the amine of Step 3 (750 mg, 3.0 mmol) in $CH_2Cl_2$ (20 mL) was added N,N-diisopropylethylamine (0.52 mL, 3.0 mmol) and upon cooling to 0° C., o-anisolyl chloride (0.44 mL, 3.0 mmol) was added dropwise. After stirring under argon for 0.5 h, the solution was concentrated in vacuo. The residue was diluted with EtOAc (75 mL), washed with 1M $KHSO_4$ (2×50 mL), sat. $NaHCO_3$ (2×50 mL), and brine (1×50 mL), and dried ($Na_2SO_4$). To a solution of the residue in MeOH/1,4-dioxane 1:1 (10 mL) was added 1M NaOH (5 mL). After stirring for 10 min. at 23° C., the solution was concentrated in vacuo. The residue was diluted with EtOAc (20 mL), washed with $H_2O$ (2×10 mL) and brine (1×10 mL) and dried ($MgSO_4$). After concentration in vacuo, the residue was purified by flash chromatography (EtOAc:hexane 2:8) to afford N-[2-(3-(2-propylamino)-3-oxo-2,2-difluoro-1-hydroxypropyl) phenyl]-2-methoxyphenylcarboxamide (475 mg, 40%) as a pink oil: MS (EI) 392 (M+), 372, 257. Anal. Calc'd. for $C_{20}H_{22}F_2N_2O_4$ plus 0.1 mol $H_2O$: C, 60.94; H, 5.68; N, 7.11. Found: C, 60.90; H, 5.78; N, 6.78.

Step 5: Preparation of N-[2-(3-(2-propylamino)-3-oxo-2,2-difluoro-1-oxopropyl)phenyl]2-methoxyphenylcarboxamide To a solution of N-[2-(3-(2-propylamino)-3-oxo-2,2-difluoro-1-hydroxypropyl)phenyl]-2-methoxyphenylcarboxamide of Step 4 (200 mg, 0.51 mmol), $CH_2Cl_2$ (5 mL) and tert-butanol (5 mL), was added 1,1,1-triacetoxy-1,1-dihydro-1,2-benziodoxyl-3(1H)-one (1.5 g, 3.54 mmol) under argon at 23° C. After 18 h, sat. $NaHCO_3$ (10 mL) was added followed by solid $Na_2S_2O_3$ (1.0 g, 6.3 mmol). After 2 h of vigorous stirring at 23° C., the organic layer was separated, washed with sat. $NaHCO_3$ (2×10 mL), sat. $Na_2S_2O_3$ (2×10 mL), and brine (1×10 mL) and dried ($MgSO_4$). Upon concentration in vacuo and trituration with ethyl ether, the title compound was afforded (100 mg) as a yellow solid : mp 131.5–132° C. $^1$H NMR ($CDCl_3$) δ1.27 (d), 4.13 (s,), 4.13–4.20 (m), 6.32 (br d), 7.04 (m), 7.10 (m), 7.19 (m), 7.51 (m) 7.67 (m), 8.11 (m), 8.22 (m), 8.90 (m), 12.01 (br s). MS (EI) 390 (M+), 254, 135. Anal. Calc'd for $C_{20}H_{20}F_2N_2O_4$ plus 0.25 mol $H_2O$: C, 60.83; H, 5.23; N, 7.09. Found: C, 60.75; H, 5.00; N, 6.95.

Biological Evaluation

The compounds of this invention exhibited antiviral activity as indicated by inhibition in vitro of herpesvirus protease and CMV infectivity. The antiviral activity of the compounds of this invention illustrated in the Examples was determined by the following methods.

Enzymatic Assay for HCMV Protease (Assemblin) Inhibitors

Assemblin protease activity was determined using a chromogenic para-nitroanilide (pNA) substrate based on the hCMV maturation cleavage site, succinyl-AGVVNA-para-nitroanilide. Incubation of this substrate with Assemblin resulted in cleavage of the alanyl para-nitroanilide amide bond, releasing free para-nitroaniline which could be determined by absorbance at 405 nm. Potential protease inhibitors were dissolved in DMSO and 10 $\mu$L were added to the wells of a 96-well plate (Dynatech, Immulon 1). Enzyme was diluted to 4.8 $\mu$g/mL in assay buffer (10 mM sodium phosphate, pH 7.4, 150 mM sodium acetate, 0.1% CHAPS, 20% glycerol) and 100 $\mu$L were added to each well. Following a 30 minute incubation at room temperature, 50 $\mu$L substrate (1 part 20 mM succinyl-AGVVNA-paranitroanilide (SEQID:1) in DMSO plus 9 parts assay buffer) were added, and periodic readings taken in a microplate reader at 405 nm relative to 650 nm. Activities were expressed as milliabsorbance unit (mAU) change per minute. Inhibitor potency was determined by comparison with incubations lacking inhibitor, which under these conditions gave an increase of 0.5–1 mAU/min. No increase was seen when enzyme was omitted. Results [$IC_{50}$ ($\mu$M)] are included in Table 1.

Assay Components:
Recombinant HCMV Protease:

HCMV protease was purified from *E. coli* expressing a DNA construction encoding the protease domain of the $U_L 80$ open reading frame of human cytomegalovirus strain AD169. The construction also encoded six additional histidine residues at the amino terminus of the protease. These additional histidine residues provided an affinity ligand by which it was purified using nickel-nitriloacetic acid-agarose (Qiagen).

The purified protease was stored as a 1–3 mg/ml stock solution in 20 mM HEPES buffer, pH 7.4; containing 20% (v/v) glycerol. This stock was diluted with assay buffer to 4.8 $\mu$g/ml. A 100 $\mu$L aliquot of this solution was used in the enzyme reaction.

A specific substrate was synthesized based on the cleavage specificity of HCMV protease at the "maturation site" of the assembly protein (F. Liu and B. Roizman, *J. Virol.*, 65, 5149 (1991), and A. Welch, et al, *J. Virol.*, 65, 4091 (1991)). The assembly protein maturation site has the sequence . . . AGVVNA*SCRLATA . . . ; the substrate used was succinyl-AGVVNA-PNA (SEQID:1) which was prepared by standard peptide synthetic methods such as that described in Bodansky and Bodansky, "The Practice of Peptide Synthesis" (1984), and was stored as a stock solution at 20 mM in dimethyl sulfoxide. This was diluted 10-fold with assay buffer to give a concentration of 2 mM just before use. An aliquot of 50 $\mu$L was used in the reaction An assay Buffer (10 mM sodium phosphate buffer, pH 7.4; 150 mM sodium acetate; 0.1% CHAPS; and 20% (v/v) glycerol) was used to dilute stock solutions of enzyme and substrate.

Antiviral Assays

These complimentary assays tested the ability of a compound to inhibit the production of new virus and the toxicity of the compound to the host cells. It was important that both assays be performed simultaneously in order to compare the results directly since, toxicity may indirectly reduce viral yield.

Abbreviations:
DMEM—Dulbecco's Modified Eagle Medium; commercially available.
FBS—fetal bovine serum; commercially available and contains unknown factors necessary for growth of cells in culture.
PBS—phosphate buffered saline: 10 mM sodium phosphate buffer, pH 7.4, 120 mM sodium chloride, 2.7 mM potassium chloride.

Viral yield was estimated by measuring the amount of a viral antigen produced 4 days post infection with a monoclonal antibody to an abundant "immediate early" viral protein. An enzyme-linked (horseradish peroxidase) secondary antibody specific to the primary (mouse) antibody was used to measure the amount of viral antigen. Test compounds were diluted to 2-times the desired final concentration in DMEM+5% FBS. One hundred microliters of this solution was placed in each well of a 96-well plate. This was performed once for the antiviral 96-well plate and again for a cytotoxicity plate. Two controls were also included for both plates; a no drug control and a no virus control. Ganciclovir was routinely tested in antiviral and cytotoxicity plates as a reference standard because it has known antiviral activity for HCMV. All cells were prepared by harvesting human foreskin fibroblasts, with trypsin and re-suspending at a concentration of $5 \times 10^5$ cells per ml in DMEM. Infected cells were prepared by infecting these with HCMV (strain AD169) at a multiplicity of infection=0.2. One hundred microliters of uninfected cells ($5 \times 10^4$ cells) were added to the appropriate wells of the cytotoxicity plate. In a similar manner 100 $\mu$l of infected cells ($5 \times 10^4$ cells) were added to the appropriate wells of the antiviral plate. Additionally, uninfected cells not treated with test compound were included as controls on the antiviral plate. Plates were incubated for 96 hours at 37° C. in 5% $CO_2$ atmosphere and processed to measure the amount of viral antigen and toxicity. Results are included in Table 1.

Enzyme Linked ImmunoSorbant Assay (ELISA) for HCMV Antigens:

The following was performed on the antiviral plate only. Media was removed and cells were fixed with 1:1 acetone:methanol for 15 minutes at −20° C. Fixative was removed and cells were washed once with PBS containing 0.05% Tween20. In order to block nonspecific binding of antibodies, each well was incubated with PBS containing 3% (w/v) bovine serum albumin (BSA) for 1 hour at 22° C. The blocking solution was removed and the cells were washed once with PBS containing 0.05% Tween20 before incubating with 1:100 dilution of primary antibody in PBS containing 3% BSA for 2 hours at 22° C. The primary antibody was a monoclonal antibody (mouse source) specific to the immediate early nuclear antigen of HCMV and was commercially available (Dupont). The 1° antibody solution was removed and the plate was rinsed 5 times with PBS containing 1% (v/v) Triton X-100 (PBST) before incubating with secondary antibody diluted 1:1000 in PBS containing 3% BSA for 2 hours at 22° C. The secondary antibody (goat source) recognized the murine-specific determinants of the 1° antibody and was covalently linked to horseradish peroxidase (Sigma). The plate was rinsed 5 times with PBST and once with deionized water before adding 100 µl TMB substrate solution and incubating 30 minutes at 22° C. The reaction was stopped by adding 100 µL of phosphoric acid and the OD at 450 nm recorded. TMB (3,3',5,5' tetramethylbenzidine) was the substrate for the horseradish peroxidase linked to the 2° antibody. It was made from a commercially available kit (Kirkegaard & Perry Laboratories, Inc.). Antiviral activity was calculated by comparing the amount of viral antigen produced in drug treated wells with that produced in wells absent of drug. Results ($EC_{50}/TD_{50}$) are included in Table 1.

Recombinant Human Cytomegalovirus Antiviral Assay

In this assay, HCMV replication was monitored by the production of *E. coli* beta-galactosidase by the engineered virus RC256 [Spaete and Mocarski, *Proc. Nat. Acad. Sci.*, 84, 7213 (1987)]. One antiviral assay and one cytotoxicity assay were done for each compound. Dilutions of test compounds and infection of cells in a 96-well plate was essentially as described above for the HCMV ELISA except for the following. Human foreskin fibroblasts at $3.5 \times 10^5$ cells per milliliter were infected in solution with RC256 at 0.05 pfu per cell. Compounds and cells were incubated 3 days and processed at 2 days post infection. For the beta galactosidase detection, the supernatant was aspirated from the antiviral assay plates and 50 µl Reporter Lysis Buffer (Promega, diluted to 1× with water) was added per well. The plates were incubated at room temperature at least 30 minutes and plates were frozen at −20° C. at this point for later processing. 50 µl of 2× assay buffer [120 mM $Na_2HPO_4$, 80 mM $NaH_2PO_4$, 2 mM $MgCl_2$, 100 mM 2-mercaptoethanol, 4.4 mM ONPG (Sigma)] was added per well and incubated at room temperature 30 to 45 minutes. The reaction was stopped with 100 µl 1M CAPS buffer, pH=11.0, per well and the optical density was read at 410 nanometers. Ganciclovir was used as a positive control and the $EC_{50}$ was determined as described above for the HCMV ELISA. Results ($EC_{50}/TD_{50}$) are included in Table 1.

Chymotrypsin Assay

The chymotrypsin assay was modified from the method of Delmar et al [*Anal. Biochem.*, 99, 316–320 (1979)]. Bovine pancreas α-chymotrypsin (type II, Sigma) was dissolved in 0.001 N HCl at 1 mg/ml and further diluted 1/600 in assay buffer (0.1 M Tris, pH 7.8, containing 0.1 M $CaCl_2$) before use. 20 µl of test compound in DMSO (or DMSO alone), 100 µl of assay buffer and 30 µl of enzyme were added to 96 well plates, mixed and pre-incubated for 30 minutes at ambient temperature. Reaction was initiated by addition of 50 µl of 0.2 mM N-succinyl-Ala-Ala-Pro-Phe-p-nitroanilide (Sigma; 2 mM in DMSO diluted 1/10 in assay buffer before use). The increase in absorbance at 405 nm was monitored for 10 minutes with a Biotek EL340 plate reader. Results are included in Table 1.

Human Leukocyte Elastase Assay

Human leukocyte elastase (HLE) (gift of R. Senior, Washington University) was dissolved in saline at 1 mg/ml and further diluted 1/20 in assay buffer (0.2 M Tris, pH 8.0) before use. 10 µl of test compound in DMSO (or DMSO alone), 100 µl of assay buffer and 50 µl of enzyme were added to 96 well plates, mixed and pre-incubated for 30 minutes at ambient temperature. Reaction was initiated by addition of 40 µl of 2.5 mM methoxysuccinyl-Ala-Ala-Pro-Val-p-nitroanilide (Sigma; 25 mM in DMSO diluted 1/10 in assay buffer before use). The increase in absorbance at 405 nm was monitored for 10 minutes with a Biotek EL340 plate reader. Results are shown in Table 1.

TABLE 1

| Example | Assemblin Protease $IC_{50}$ (µM) or % @ Conc. (µM) | Antiviral Activity ($EC_{50}/TD_{50}$)(µM) | Chymotrypsin % @ Conc. (µM) | HLE % @ Conc. (µM) |
|---|---|---|---|---|
| 1 | 7.7 | RC256 45/>100 | 0% @ 300 | 25% @ 300 |
| 2 | 5.3 | RC256 57/>100 | 48% @ 100 | 26% @ 100 |
| 4 | 49 | | 11% @ 100 | |
| 5 | 3.7 | RC256 55/>100 | 0% @ 300 | |
| 6 | 17 | | 21% @ 100 | |
| 7 | 84% @ 33 | ELISA 16/>100 | 27% @ 100 | |
| 8 | 18% @ 33 | | | |
| 9 | 26 | RC256 30/>100 | 48% @ 100 | |
| 10 | 39% @ 10 | ELISA >100/>100 | 49% @ 100 | |
| 11 | 40% @ 33 | | | |
| 12 | 14% @ 33 | | | |
| 13 | 8.3 | 28/>100 | 39% @ 32 | 50% @ 24 |
| 15 | 30% @ 100 | | | |
| 16 | 36 | | | |
| 17 | 8.5 | | 0% @ 300 | |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

For infections of the eye or other external tissues, e.g., mouth and skin, the formulations are preferably applied as a topical ointment or cream containing the active ingredient (s) in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiviral active ingredients are preferably present in such formulations in a concentration of 0.5 to 20%, advantageously 0.5 to 10% and particularly about 1.5% w/w.

Although this invention has been described with respect to specific embodiments, the details of these embodiments are not to be construed as limitations.

What is claimed is:

1. A compound of Formula I:

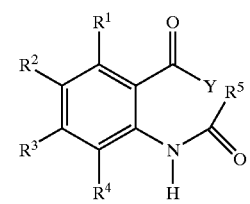

wherein each of $R^1$, $R^2$, $R^3$, and $R^4$ is independently selected from hydrido, alkyl, aralkyl, halo, alkoxy, cyano, nitro, amino, alkylamino, N-acylamino, alkylsulfonyloxy, amino sulfonyl, N-(haloalkylcarbonyl)amino, peptidyl, amino acid residue,

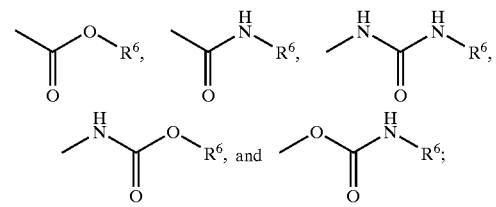

wherein $R^5$ is selected from alkoxy, aryloxy, aralkyloxy, alkylthio, arylthio, aralkylthio, alkylamino, arylamino, aralkylamino, alkyl, aryl, aralkyl, and heterocyclylalkyl, wherein $R^5$ is optionally substituted at a substitutable position with one or more substituents selected from alkyl, alkoxy, aryloxy, alkylthio, arylthio, halo, nitro, N-acylamino, amino, alkylamino, alkoxycarbonyl, amino acid residue and peptidyl;

wherein $R^6$ is selected from alkyl, aryl, aralkyl, heterocyclyl and heterocyclylalkyl, wherein $R^6$ is optionally substituted at a substitutable position with a radical selected from alkoxy, aryloxy, alkylthio, arylthio, halo, nitro, N-acylamino, amino, alkylamino and alkoxycarbonyl;

wherein Y is selected from fluoroalkyl and

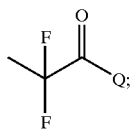

wherein Q is selected from alkoxy, aryloxy, aralkyloxy, amino acid residue, peptidyl, and —NHR⁷; and wherein R⁷ is a radical selected from alkyl, aralkyl, and heterocyclylalkyl, wherein R⁷ is optionally substituted at a substitutable position with a radical selected from amino, nitrogen-containing heterocyclyl and alkylamino;

or a pharmaceutically-acceptable salt or tautomer thereof.

2. Compound of claim 1 wherein each of $R^1$, $R^2$, $R^3$, and $R^4$ is independently selected from hydrido, lower alkyl, lower aralkyl, halo, lower alkoxy, cyano, nitro, amino, lower alkylamino, N-acylamino, lower alkylsulfonyloxy, aminosulfonyl, lower N-(haloalkylcarbonyl)amino, amino acid residue, peptidyl,

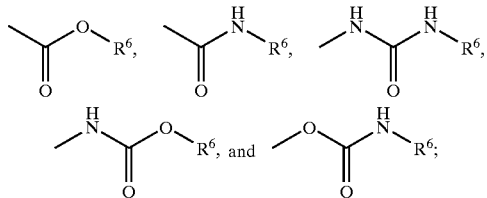

wherein R⁵ is selected from lower alkoxy, phenyloxy, lower aralkyloxy, lower alkylthio, phenylthio, lower aralkylthio, lower alkylamino, arylamino, lower aralkylamino, lower alkyl, 6–10-membered aryl, lower aralkyl, and lower heterocyclylalkyl, wherein R⁵ is optionally substituted at a substitutable position with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue and peptidyl; wherein R⁶ is selected from lower alkyl, 6–10-membered aryl, lower aralkyl, 5–10-membered heterocyclyl and lower heterocyclylalkyl, wherein R⁶ is optionally substituted at a substitutable position with a radical selected from lower alkoxy, phenyloxy, lower alkylthio, phenylthio, halo, nitro, N-acylamino, amino, lower alkylamino, and lower alkoxycarbonyl; wherein Y is selected from lower fluoroalkyl and

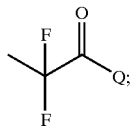

wherein Q is selected from lower alkoxy, phenyloxy, lower aralkyloxy, N-amino acid residue, N-peptidyl, and —NHR⁷; and wherein R⁷ is a radical selected from lower alkyl, lower aralkyl, and lower heterocyclylalkyl, wherein R⁷ is optionally substituted at a substitutable position with one or more radical selected from amino, 5–6-membered nitrogen-containing heterocyclyl and lower N,N-dialkylamino; or a pharmaceutically-acceptable salt or tautomer thereof.

3. Compound of claim 2 wherein Y is lower fluoroalkyl; wherein each of $R^1$, $R^2$, $R^3$, and $R^4$ is independently selected from hydrido, lower alkyl, halo, lower alkoxy, nitro, and amino; and wherein R⁵ is selected from phenylalkoxy, lower alkyl substituted with halo or phenyloxy, phenyl, lower phenylalkyl, and five–ten membered heteroaryl, wherein R⁵ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

4. Compound of claim 3 wherein Y is selected from difluoromethyl, trifluoromethyl, pentafluoroethyl, heptafluoropropyl, 1,1-difluoroethyl, and 1,1-difluoropropyl; wherein each of $R^1$, $R^2$, $R^3$, and $R^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; wherein R⁵ is selected from phenylmethoxy, phenylethoxy, phenylpropoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein R⁵ is optionally substituted at a substitutable position of a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, phenyloxy, methylthio, phenylthio, fluoro, chloro, bromo, iodo, nitro, N-formylamino, acetylamino, amino, N,N-dimethylamino and methoxycarbonyl; or a pharmaceutically-acceptable salt or tautomer thereof.

5. Compound of claim 2 wherein Y is:

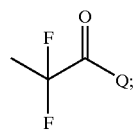

wherein Q is selected from lower alkoxy, phenyloxy, lower aralkyloxy, N-amino acid residue, N-peptidyl, and —NHR⁷; and wherein R⁷ is a radical selected from lower alkyl, lower aralkyl, and lower heteroaralkyl, wherein R⁷ is optionally substituted at a substitutable position with a radical selected from amino, 5–6 membered nitrogen-containing heterocyclyl and lower N,N-dialkylamino; wherein each of $R^1$, $R^2$, $R^3$, and $R^4$ is independently selected from hydrido, lower alkyl, halo, lower alkoxy, nitro, and amino; and wherein R⁵ is selected from phenylalkoxy, lower alkyl substituted with halo or phenyloxy, phenyl, lower phenylalkyl, and five–ten membered heteroaryl, wherein R⁵ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

6. Compound of claim 5 wherein Y is:

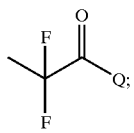

wherein Q is selected from methoxy, ethoxy, propoxy, isopropoxy, butoxy, phenyloxy, benzyloxy, phenylethoxy, and —NHR$^7$; and wherein R$^7$ is a radical selected from methyl, ethyl, n-propyl, isopropyl, n-butyl, isobutyl, sec-butyl, tert-butyl, pentyl, hexyl, benzyl, phenethyl, oxazolylmethyl, oxazolylethyl, imidazolylmethyl, imidazolylethyl, oxazolinylmethyl, oxazolinylethyl, indolylethyl, indolylmethyl, pyridylmethyl, thienylmethyl, and furylethyl, wherein R$^7$ is optionally substituted at a substitutable position with a radical selected from amino, piperidinyl, piperazinyl, pyrrolidinyl, morpholinyl, pyridyl, pyrimidyl and N,N-dimethylamino; wherein each of R$^1$, R$^2$, R$^3$, and R$^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; and wherein R$^5$ is selected from phenylmethoxy, phenylethoxy, phenylpropoxy, fluoromethyl, difluoromethyl, trifluoromethyl, chloromethyl, dichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein R$^5$ is optionally substituted at a substitutable position on a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, tert-butoxy, phenyloxy, methylthio, phenylthio, fluoro, chloro, bromo, iodo, nitro, N-formylamino, N-acetylamino, amino, N,N-dimethylamino and methoxycarbonyl; or a pharmaceutically-acceptable salt or tautomer thereof.

7. A pharmaceutical composition comprising a therapeutically-effective amount of a compound and a pharmaceutically-acceptable carrier or diluent, said compound selected from a compound of Formula I:

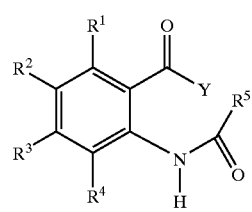

wherein each of R$^1$, R$^2$, R$^3$, and R$^4$ is independently selected from hydrido, alkyl, aralkyl, halo, alkoxy, cyano, nitro, amino, alkylamino, N-acylamino, alkylsulfonyloxy, aminosulfonyl, N-(haloalkylcarbonyl)amino, peptidyl, amino acid residue,

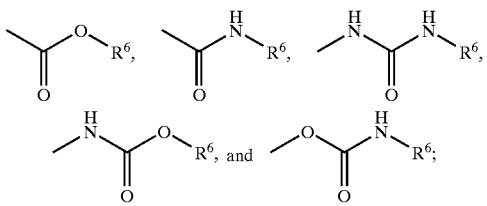

wherein R$^5$ is selected from alkoxy, aryloxy, aralkyloxy, alkylthio, arylthio, aralkylthio, alkylamino, arylamino, aralkylamino, alkyl, aryl, aralkyl, and heterocyclylalkyl, wherein R$^5$ is optionally substituted at a substitutable position with one or more substituents selected from alkyl, alkoxy, aryloxy, alkylthio, arylthio, halo, nitro, N-acylamino, amino, alkylamino, alkoxycarbonyl, amino acid residue and peptidyl;

wherein R$^6$ is selected from alkyl, aryl, aralkyl, heterocyclyl and heterocyclylalkyl, wherein R$^6$ is optionally substituted at a substitutable position with a radical selected from alkoxy, aryloxy, alkylthio, arylthio, halo, nitro, N-acylamino, amino, alkylamino and alkoxycarbonyl;

wherein Y is selected from fluoroalkyl and

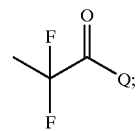

wherein Q is selected from alkoxy, aryloxy, aralkyloxy, amino acid residue, peptidyl, and —NHR$^7$; and wherein R$^7$ is a radical selected from alkyl, aralkyl, and heterocyclylalkyl, wherein R$^7$ is optionally substituted at a substitutable position with a radical selected from amino, nitrogen-containing heterocyclyl and alkylamino;

or a pharmaceutically-acceptable salt or tautomer thereof.

8. A pharmaceutical composition of claim 7 wherein each of R$^1$, R$^2$, R$^3$, and R$^4$ is independently selected from hydrido, lower alkyl, lower aralkyl, halo, lower alkoxy, cyano, nitro, amino, lower alkylamino, N-acylamino, lower alkylsulfonyloxy, amino sulfonyl, lower N-(haloalkylcarbonyl)amino, amino acid residue, peptidyl,

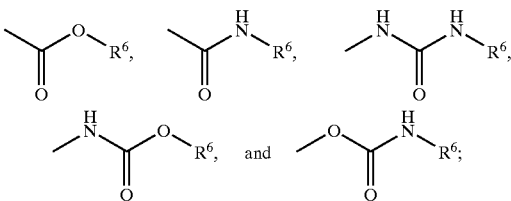

wherein R$^5$ is selected from lower alkoxy, phenyloxy, lower aralkyloxy, lower alkylthio, phenylthio, lower aralkylthio, lower alkylamino, arylamino, lower aralkylamino, lower alkyl, 6–10-membered aryl, lower aralkyl, and lower heterocyclylalkyl, wherein R$^5$ is optionally substituted at a substitutable position with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue and peptidyl; wherein R⁶ is selected from lower alkyl, 6–10-membered aryl, lower aralkyl, 5–10-membered heterocyclyl and lower heterocyclylalkyl, wherein R⁶ is optionally substituted at a substitutable position with a radical selected from lower alkoxy, phenyloxy, lower alkylthio, phenylthio, halo, nitro, N-acylamino, amino, lower alkylamino, and lower alkoxycarbonyl; wherein Y is selected from lower fluoroalkyl and

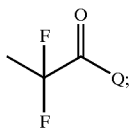

wherein Q is selected from lower alkoxy, phenyloxy, lower aralkyloxy, N-amino acid residue, N-peptidyl, and —NHR⁷; and wherein R⁷ is a radical selected from lower alkyl, lower aralkyl, and lower heterocyclylalkyl, wherein R⁷ is optionally substituted at a substitutable position with one or more radical selected from amino, 5–6-membered nitrogen-containing heterocyclyl and lower N,N-dialkylamino; or a pharmaceutically-acceptable salt or tautomer thereof.

9. A pharmaceutical composition of claim 8 wherein Y is lower fluoroalkyl; wherein each of R¹, R², R³, and R⁴ is independently selected from hydrido, lower alkyl, halo, lower alkoxy, nitro, and amino; and wherein R⁵ is selected from phenylalkoxy, lower alkyl substituted with halo or phenyloxy, phenyl, lower phenylalkyl, and five–ten membered heteroaryl, wherein R⁵ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

10. A pharmaceutical composition of claim 9 wherein Y is selected from difluoromethyl, trifluoromethyl, pentafluoroethyl, heptafluoropropyl, 1,1-difluoroethyl, and 1,1-difluoropropyl; wherein each of R¹, R², R³, and R⁴ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; wherein R⁵ is selected from phenylmethoxy, phenylethoxy, phenylpropoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein R⁵ is optionally substituted at a substitutable position of a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, phenyloxy, methylthio, phenylthio, fluoro, chloro, bromo, iodo, nitro, N-formylamino, acetylamino, amino, N,N-dimethylamino and methoxycarbonyl; or a pharmaceutically-acceptable salt or tautomer thereof.

11. A pharmaceutical composition of claim 8 wherein Y is:

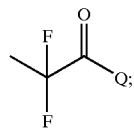

wherein Q is selected from lower alkoxy, phenyloxy, lower aralkyloxy, N-amino acid residue, N-peptidyl, and —NHR⁷; and wherein R⁷ is a radical selected from lower alkyl, lower aralkyl, and lower heteroaralkyl, wherein R⁷ is optionally substituted at a substitutable position with a radical selected from amino, 5–6 membered nitrogen-containing heterocyclyl and lower N,N-dialkylamino; wherein each of R¹, R², R³, and R⁴ is independently selected from hydrido, lower alkyl, halo, lower alkoxy, nitro, and amino; and wherein R⁵ is selected from phenylalkoxy, lower alkyl substituted with halo or phenyloxy, phenyl, lower phenylalkyl, and five–ten membered heteroaryl, wherein R⁵ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

12. A pharmaceutical composition of claim 11 wherein Y is:

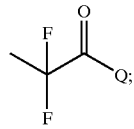

wherein Q is selected from methoxy, ethoxy, propoxy, isopropoxy, butoxy, phenyloxy, benzyloxy, phenylethoxy, and —NHR⁷; and wherein R⁷ is a radical selected from methyl, ethyl, n-propyl, isopropyl, n-butyl, isobutyl, sec-butyl, tert-butyl, pentyl, hexyl, benzyl, phenethyl, oxazolylmethyl, oxazolylethyl, imidazolylmethyl, imidazolylethyl, oxazolinylmethyl, oxazolinylethyl, indolylethyl, indolylmethyl, pyridylmethyl, thienylmethyl, and furylethyl, wherein R⁷ is optionally substituted at a substitutable position with a radical selected from amino, piperidinyl, piperazinyl, pyrrolidinyl, morpholinyl, pyridyl, pyrimidyl and N,N-dimethylamino; wherein each of R¹, R², R³, and R⁴ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; and wherein R⁵ is selected from phenylmethoxy, phenylethoxy, phenylpropoxy, fluoromethyl, difluoromethyl, trifluoromethyl, chloromethyl, dichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein R⁵ is optionally substituted at a substitutable position on a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, tert-butoxy, phenyloxy, methylthio, phenylthio, fluoro, chloro, bromo, iodo, nitro, N-formylamino, N-acetylamino, amino, N,N- dimethylamino and methoxycarbonyl; or a pharmaceutically-acceptable salt or tautomer thereof.

13. A method of treating herpes viral infection in a subject, said method comprising treating said subject with an effective amount of a compound of Formula I:

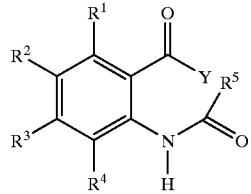

wherein each of $R^1$, $R^2$, $R^3$, and $R^4$ is independently selected from hydrido, alkyl, aralkyl, halo, alkoxy, cyano, nitro, amino, alkylamino, N-acylamino, alkylsulfonyloxy, aminosulfonyl, N-(haloalkylcarbonyl)amino, peptidyl, amino acid residue,

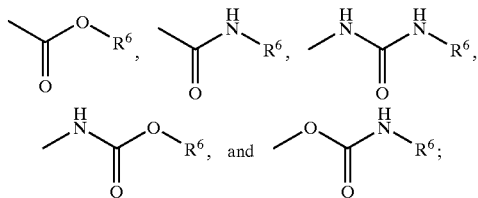

wherein $R^5$ is selected from alkoxy, aryloxy, aralkyloxy, alkylthio, arylthio, aralkylthio, alkylamino, arylamino, aralkylamino, alkyl, aryl, aralkyl, and heterocyclylalkyl, wherein $R^5$ is optionally substituted at a substitutable position with one or more substituents selected from alkyl, alkoxy, aryloxy, alkylthio, arylthio, halo, nitro, N-acylamino, amino, alkylamino, alkoxycarbonyl, amino acid residue and peptidyl;

wherein $R^6$ is selected from alkyl, aryl, aralkyl, heterocyclyl and heterocyclylalkyl, wherein $R^6$ is optionally substituted at a substitutable position with a radical selected from alkoxy, aryloxy, alkylthio, arylthio, halo, nitro, N-acylamino, amino, alkylamino and alkoxycarbonyl;

wherein Y is selected from fluoroalkyl and

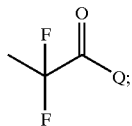

wherein Q is selected from alkoxy, aryloxy, aralkyloxy, amino acid residue, peptidyl, and —NHR$^7$; and wherein $R^7$ is a radical selected from alkyl, aralkyl, and heterocyclylalkyl, wherein $R^7$ is optionally substituted at a substitutable position with a radical selected from amino, nitrogen-containing heterocyclyl and alkylamino;

or a pharmaceutically-acceptable salt or tautomer thereof.

14. A method of claim 13 wherein each of $R^1$, $R^2$, $R^3$, and $R^4$ is independently selected from hydrido, lower alkyl, lower aralkyl, halo, lower alkoxy, cyano, nitro, amino, lower alkylamino, N-acylamino, lower alkylsulfonyloxy, aminosulfonyl, lower N-(haloalkylcarbonyl)amino, amino acid residue, peptidyl,

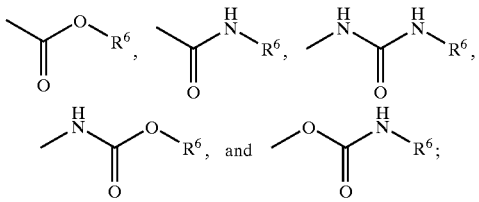

wherein $R^5$ is selected from lower alkoxy, phenyloxy, lower aralkyloxy, lower alkylthio, phenylthio, lower aralkylthio, lower alkylamino, arylamino, lower aralkylamino, lower alkyl, 6–10-membered aryl, lower aralkyl, 5–10-membered heterocyclyl, and lower heterocyclylalkyl, wherein $R^5$ is optionally substituted at a substitutable position with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue and peptidyl; wherein $R^6$ is selected from lower alkyl, 6–10-membered aryl, lower aralkyl, 5–10-membered heterocyclyl and lower heterocyclylalkyl, wherein $R^6$ is optionally substituted at a substitutable position with a radical selected from lower alkoxy, phenyloxy, lower alkylthio, phenylthio, halo, nitro, N-acylamino, amino, lower alkylamino, and lower alkoxycarbonyl; wherein Y is selected from lower fluoroalkyl and

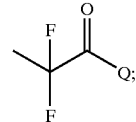

wherein Q is selected from lower alkoxy, phenyloxy, lower aralkyloxy, N-amino acid residue, N-peptidyl, and —NHR$^7$; and wherein $R^7$ is a radical selected from lower alkyl, lower aralkyl, and lower heterocyclylalkyl, wherein $R^7$ is optionally substituted at a substitutable position with one or more radical selected from amino, 5–6-membered nitrogen-containing heterocyclyl and lower N,N-dialkylamino; or a pharmaceutically-acceptable salt or tautomer thereof.

15. A method of claim 14 wherein Y is lower fluoroalkyl; wherein each of $R^1$, $R^2$, $R^3$, and $R^4$ is independently selected from hydrido, lower alkyl, halo, lower alkoxy, nitro, and amino; and wherein $R^5$ is selected from phenylalkoxy, lower alkyl substituted with halo or phenyloxy, phenyl, lower phenylalkyl, and five–ten membered heteroaryl, wherein $R^5$ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

16. A method of claim 15 wherein Y is selected from difluoromethyl, trifluoromethyl, pentafluoroethyl, heptafluoropropyl, 1,1-difluoroethyl, and 1,1-difluoropropyl; wherein each of $R^1$, $R^2$, $R^3$, and $R^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; wherein $R^5$ is selected from phenylmethoxy, phenylethoxy, phenylpropoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein $R^5$ is optionally substituted at a substitutable position of a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, phenyloxy, methylthio, phenylthio, fluoro, chloro, bromo, iodo, nitro, N-formylamino, acetylamino, amino, N,N-dimethylamino and methoxycarbonyl; or a pharmaceutically-acceptable salt or tautomer thereof.

17. A method of claim 14 wherein Y is:

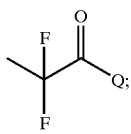

wherein Q is selected from lower alkoxy, phenyloxy, lower aralkyloxy, N-amino acid residue, N-peptidyl, and —NHR$^7$; and wherein $R^7$ is a radical selected from lower alkyl, lower aralkyl, and lower heteroaralkyl, wherein $R^7$ is optionally substituted at a substitutable position with a radical selected from amino, 5–6 membered nitrogen-containing heterocyclyl and lower N,N-dialkylamino; wherein each of $R^1$, $R^2$, $R^3$, and $R^4$ is independently selected from hydrido, lower alkyl, halo, lower alkoxy, nitro, and amino; and wherein $R^5$ is selected from phenylalkoxy, lower alkyl substituted with halo or phenyloxy, phenyl, lower phenylalkyl, and five–ten membered heteroaryl, wherein $R^5$ is optionally substituted at a substitutable position of a phenyl or heteroaryl radical with one or more substituents selected from lower alkyl, lower alkoxy, phenyloxy, lower alkylthio, phenylthio, halo, nitro, N-acylamino, amino, lower alkylamino, lower alkoxycarbonyl, amino acid residue, and peptidyl; or a pharmaceutically-acceptable salt or tautomer thereof.

18. A method of claim 17 wherein Y is:

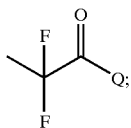

wherein Q is selected from methoxy, ethoxy, propoxy, isopropoxy, butoxy, phenyloxy, benzyloxy, phenylethoxy, and —NHR$^7$; and wherein $R^7$ is a radical selected from methyl, ethyl, n-propyl, isopropyl, n-butyl, isobutyl, sec-butyl, tert-butyl, pentyl, hexyl, benzyl, phenethyl, oxazolylmethyl, oxazolylethyl, imidazolylmethyl, imidazolylethyl, oxazolinylmethyl, oxazolinylethyl, indolylethyl, indolylmethyl, pyridylmethyl, thienylmethyl, and furylethyl, wherein $R^7$ is optionally substituted at a substitutable position with a radical selected from amino, piperidinyl, piperazinyl, pyrrolidinyl, morpholinyl, pyridyl, pyrimidyl and N,N-dimethylamino; wherein each of $R^1$, $R^2$, $R^3$, and $R^4$ is independently selected from hydrido, methyl, ethyl, n-propyl, isopropyl, n-butyl, isobutyl, sec-butyl, tert-butyl, pentyl, hexyl, fluoro, chloro, bromo, iodo, methoxy, ethoxy, propoxy, isopropoxy, butoxy, tert-butoxy, nitro, and amino; and wherein $R^5$ is selected from phenylmethoxy, phenylethoxy, phenylpropoxy, fluoromethyl, difluoromethyl, trifluoromethyl, chloromethyl, dichloromethyl, pentafluoroethyl, heptafluoropropyl, difluorochloromethyl, dichlorofluoromethyl, difluoroethyl, difluoropropyl, dichloroethyl, dichloropropyl, phenyloxyethyl, phenyloxypropyl, phenyl, phenylmethyl, and phenylethyl, wherein $R^5$ is optionally substituted at a substitutable position on a phenyl or heteroaryl radical with one or more substituents selected from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, tert-butoxy, phenyloxy, methylthio, phenylthio, fluoro, chloro, bromo, iodo, nitro, N-formylamino, N-acetylamino, amino, N,N-dimethylamino and methoxycarbonyl; or a pharmaceutically-acceptable salt or tautomer thereof.

19. The method of claim 13 wherein the subject is infected with a herpesvirus selected from herpes simplex virus type-1 (HSV-1), herpes simplex virus type-2 (HSV-2), cytomegalovirus (CMV), varicella-zoster virus (VZV), Epstein-Barr virus, herpesvirus-6 (HHV-6), herpesvirus-7 (HHV-7), herpesvirus-8 (HHV-8), pseudorabies and rhinotracheitis.

20. A method of inhibiting a viral protease, said method comprising treating said subject with an effective amount of a compound of claim 1.

21. Method of claim 19 wherein the viral protease is a herpesvirus protease.

22. Method of claim 21 wherein the viral protease is selected from a CMV protease, an HSV-1 protease and a HSV-2 protease.

23. Method of claim 22 wherein the viral protease is a CMV protease, encoded by $U_L80$.

24. A method of prophylactic treatment of herpes viral infection in a subject, said method comprising treating said subject with an effective amount of a compound of claim 1.

25. The method of claim 24 wherein the herpesvirus is selected from herpes simplex virus type-1 (HSV-1), herpes simplex virus type-2 (HSV-2), cytomegalovirus (CMV), varicella-zoster virus (VZV), Epstein-Barr virus, herpesvirus-6 (HHV-6), herpesvirus-7 (HHV-7), herpesvirus-8 (HHV-8), pseudorabies and rhinotracheitis.

26. A compound of Formula I

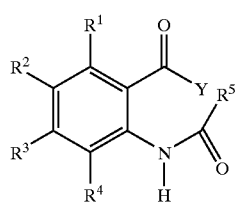

I wherein each of $R^1$, $R^2$, $R^3$, and $R^4$ is independently selected from hydrido, alkyl, aralkyl, halo, alkoxy, cyano, nitro, amino, alkylamino, N-acylamino, alkylsulfonyloxy, aminosulfonyl, N-(haloalkylcarbonyl)amino, peptidyl, amino acid residue,

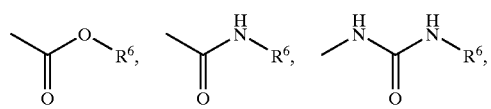

-continued

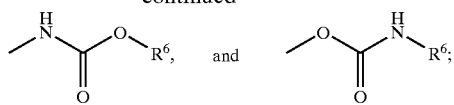

wherein R⁵ is selected from alkoxy, aryloxy, aralkyloxy, alkylthio, arylthio, aralkylthio, alkylamino, arylamino, aralkylamino, alkyl, aryl, aralkyl, heterocyclyl, and heterocyclylalkyl, wherein R⁵ is optionally substituted at a substitutable position with one or more substituents selected from alkyl, alkoxy, aryloxy, alkylthio, arylthio, halo, nitro, N-acylamino, amino, alkylamino, alkoxycarbonyl, amino acid residue and peptidyl;

wherein R⁶ is selected from alkyl, aryl, aralkyl, heterocyclyl and heterocyclylalkyl, wherein R⁶ is optionally substituted at a substitutable position with a radical selected from alkoxy, aryloxy, alkylthio, arylthio, halo, nitro, N-acylamino, amino, alkylamino and alkoxycarbonyl;

wherein Y is selected from fluoroalkyl and

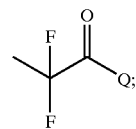

wherein Q is selected from alkoxy, aryloxy, aralkyloxy, amino acid residue, peptidyl, and —NHR⁷; and wherein R⁷ is a radical selected from alkyl, aralkyl, and heterocyclylalkyl, wherein R⁷ is optionally substituted at a substitutable position with a radical selected from amino, nitrogen-containing heterocyclyl and alkylamino;

or a pharmaceutically-acceptable salt or tautomer thereof.

\* \* \* \* \*